(12) United States Patent
Iwashita et al.

(10) Patent No.: US 11,160,782 B2
(45) Date of Patent: Nov. 2, 2021

(54) METHOD FOR PRODUCING NOBILETIN-CONTAINING SOLID DISPERSION

(71) Applicant: KAO CORPORATION, Tokyo (JP)

(72) Inventors: Masazumi Iwashita, Omiya-ku (JP); Masahiro Umehara, Sumida-ku (JP); Shintaro Onishi, Utsunomiya (JP); Masaki Yamamoto, Utsunomiya (JP); Keisuke Yamagami, Kamisu (JP); Takaaki Ishigami, Izumisano (JP)

(73) Assignee: KAO CORPORATION, Tokyo (JP)

(*) Notice: Subject to any disclaimer, the term of this patent is extended or adjusted under 35 U.S.C. 154(b) by 0 days.

(21) Appl. No.: 16/322,601

(22) PCT Filed: Aug. 1, 2017

(86) PCT No.: PCT/JP2017/027923
§ 371 (c)(1),
(2) Date: Feb. 1, 2019

(87) PCT Pub. No.: WO2018/025871
PCT Pub. Date: Feb. 8, 2018

(65) Prior Publication Data
US 2019/0183852 A1    Jun. 20, 2019

(30) Foreign Application Priority Data

Aug. 4, 2016  (JP) .............................. JP2016-153635
Feb. 14, 2017 (JP) .............................. JP2017-025302

(51) Int. Cl.
| | | |
|---|---|---|
| *A61K 31/353* | (2006.01) | |
| *A61P 25/00* | (2006.01) | |
| *A61P 3/00* | (2006.01) | |
| *A61K 31/352* | (2006.01) | |
| *A61P 43/00* | (2006.01) | |
| *A61P 25/28* | (2006.01) | |
| *A23L 33/10* | (2016.01) | |
| *A23L 33/105* | (2016.01) | |
| *A61K 9/10* | (2006.01) | |
| *A61K 47/22* | (2006.01) | |
| *A61K 47/26* | (2006.01) | |

(52) U.S. Cl.
CPC ............ *A61K 31/353* (2013.01); *A23L 33/10* (2016.08); *A23L 33/105* (2016.08); *A61K 9/10* (2013.01); *A61K 31/352* (2013.01); *A61P 3/00* (2018.01); *A61P 25/00* (2018.01); *A61P 25/28* (2018.01); *A61P 43/00* (2018.01); *A23V 2002/00* (2013.01); *A61K 47/22* (2013.01); *A61K 47/26* (2013.01)

(58) Field of Classification Search
CPC ......... A61K 31/353; A61K 9/10; A61K 47/26
USPC ........................................................ 514/25
See application file for complete search history.

(56) References Cited

U.S. PATENT DOCUMENTS

| | | |
|---|---|---|
| 2007/0213282 A1 | 9/2007 | Sasaki |
| 2015/0335673 A1 | 11/2015 | Yamada |
| 2017/0273999 A1 | 9/2017 | Umehara et al. |

FOREIGN PATENT DOCUMENTS

| | | | |
|---|---|---|---|
| CN | 104884054 A | | 9/2015 |
| CN | 104902764 A | | 9/2015 |
| JP | 11-169148 A | | 6/1999 |
| JP | 2002-60340 A | | 2/2002 |
| JP | 2009007336 A | * | 1/2009 |
| JP | 2011105714 A | * | 6/2011 |
| JP | 2014-125461 A | | 7/2014 |
| WO | WO 2006/049234 A1 | | 5/2006 |
| WO | WO 2016/031651 A1 | | 3/2016 |

OTHER PUBLICATIONS

Zhang et al. (Journal of Enzyme Inhibition and Medicinal Chemistry, Feb. 2007; 22(1): 83-90).*
Itoh et al. (Biological & Pharmaceutical Bulletin (2009), 32(3), 410-415) (abstract sent).*
Onike et al. (Journal of Pharmacy and Pharmacology. Journal of Pharmacy and Pharmacology, Oct. 2010 62(10):1476-1477) (abstract sent).*
Nakajima et al.; JP 2009007336 A; Jan. 15, 2009 (Machine-English Translation).*
Kagawa et al.; JP 2011105714 A; Jun. 2, 2011 (Machine-English Translation).*
Stanojevic et al. (Arch Oncol 2004;12(4):203-5).*
International Search Report dated Sep. 19, 2017 in PCT/JP2017/027923 filed on Aug. 1, 2017.
Takashi, S., "Does Alzheimer one disease improve in the peel of a mandarin orange? Clinical response of the N dried orange peel to the cognitive functional disorder of Alzheimer one disease," Journal of Pharmacological Sciences, 2015, vol. 145, pp. 234-236 (4 total pages with English Abstract).
Onoue, S. et al., "Development of High-Energy Amorphous Solid Dispersion of Nanosized Nobiletin, a Citrus Polymethoxylated Flavone, with Improved Oral Bioavailability," Journal of Pharmacological Sciences, vol. 100, No. 9, Sep. 2011, pp. 3793-3801.
Onoue, S. et al., "Physicochemical and biopharmaceutical characterization of amorphous solid dispersion of nobiletin, a citrus polymethoxylated flavone, with improved hepatoprotective effects," European Journal of Pharmaceutical Sciences, vol. 49, No. 4, May 2013, pp. 453-460.

* cited by examiner

*Primary Examiner* — Shaojia A Jiang
*Assistant Examiner* — Michael C Henry
(74) *Attorney, Agent, or Firm* — Oblon, McClelland, Maier & Neustadt, L.L.P.

(57) ABSTRACT

A nobiletin composition having high water solubility and a method for easily producing the same are provided. A method for producing a solid dispersion comprising nobiletin, comprising the step of mixing nobiletin or a nobiletin-containing product with a water-soluble hesperidin derivative, and then melting the mixture by heating; and the step of solidifying the melted product by cooling. A nobiletin-containing composition produced by the method.

17 Claims, 23 Drawing Sheets

METHOD FOR PRODUCING NOBILETIN-CONTAINING SOLID DISPERSION

FIELD OF THE INVENTION

The present invention relates to a method for producing a nobiletin-containing solid dispersion.

BACKGROUND OF THE INVENTION

Nobiletin is one of polymethoxy flavonoids contained in citrus, such as satsuma orange and shequasar. Nobiletin is recognized as an essential ingredient of health food products because it has a variety of bioactivities, such as PPAR activation and promotion of adiponectin secretion (Patent Literature 1), promotion of neurite outgrowth (Patent Literature 2), and suppression of memory disorder (Non Patent Literature 1).

However, nobiletin is poorly water-soluble, and it is difficult to effectively utilize the physiological function of its bulk substance as it is in applications of food and beverage products, pharmaceuticals, and the like.

For this reason, techniques of dissolving nobiletin in water have been examined, and a method of preparing a cyclodextrin inclusion compound has been reported, for example (Patent Literature 3). In this production method, however, use of an aqueous ethanol solution as a solvent leads to problems, such as the complication of the process caused by the removal of the solvent, and thus increased cost, and insufficient water-solubility.

Moreover, it is reported that the solubility of poorly water-soluble polyphenols in water is increased when the poorly water-soluble polyphenols are mixed with a water-soluble polyphenol, are melted by heating, and are solidified by cooling (Patent Literature 4). However, the solubilization of nobiletin is not found in the literature, and the effect thereof has not been clarified.

[Patent Literature 1] WO 2006/049234
[Patent Literature 2] JP-A-2002-60340
[Patent Literature 3] JP-A-11-169148
[Patent Literature 4] JP-A-2014-125461
[Non Patent Literature 1] Journal of Pharmacological Sciences, 2015, 145, 234-236

SUMMARY OF THE INVENTION

The present invention is characterized by the following (1) to (5).
(1) A method for producing a solid dispersion comprising nobiletin, comprising the step of mixing nobiletin or a nobiletin-containing product with a water-soluble hesperidin derivative, and then melting the mixture by heating; and the step of solidifying the melted product by cooling.
(2) A nobiletin-containing solid dispersion comprising nobiletin or a nobiletin-containing product, and a water-soluble hesperidin derivative, wherein nobiletin having a degree of crystallization of 10% or less as calculated from an X-ray diffraction spectrum is dispersed.
(3) A nobiletin-containing solid dispersion comprising nobiletin or a nobiletin-containing product, and a water-soluble hesperidin derivative, wherein nobiletin is dispersed and has a degree of crystallization of 10% or less as calculated from an X-ray diffraction spectrum.
(4) A nobiletin-containing solid dispersion obtained by the method according to (1), wherein nobiletin has a degree of crystallization of 10% or less as calculated from an X-ray diffraction spectrum.
(5) A food or beverage product, a pharmaceutical or a quasi-drug, comprising the nobiletin-containing solid dispersion according to any one of (2) to (4).

DETAILED DESCRIPTION OF THE INVENTION

Figure 1:
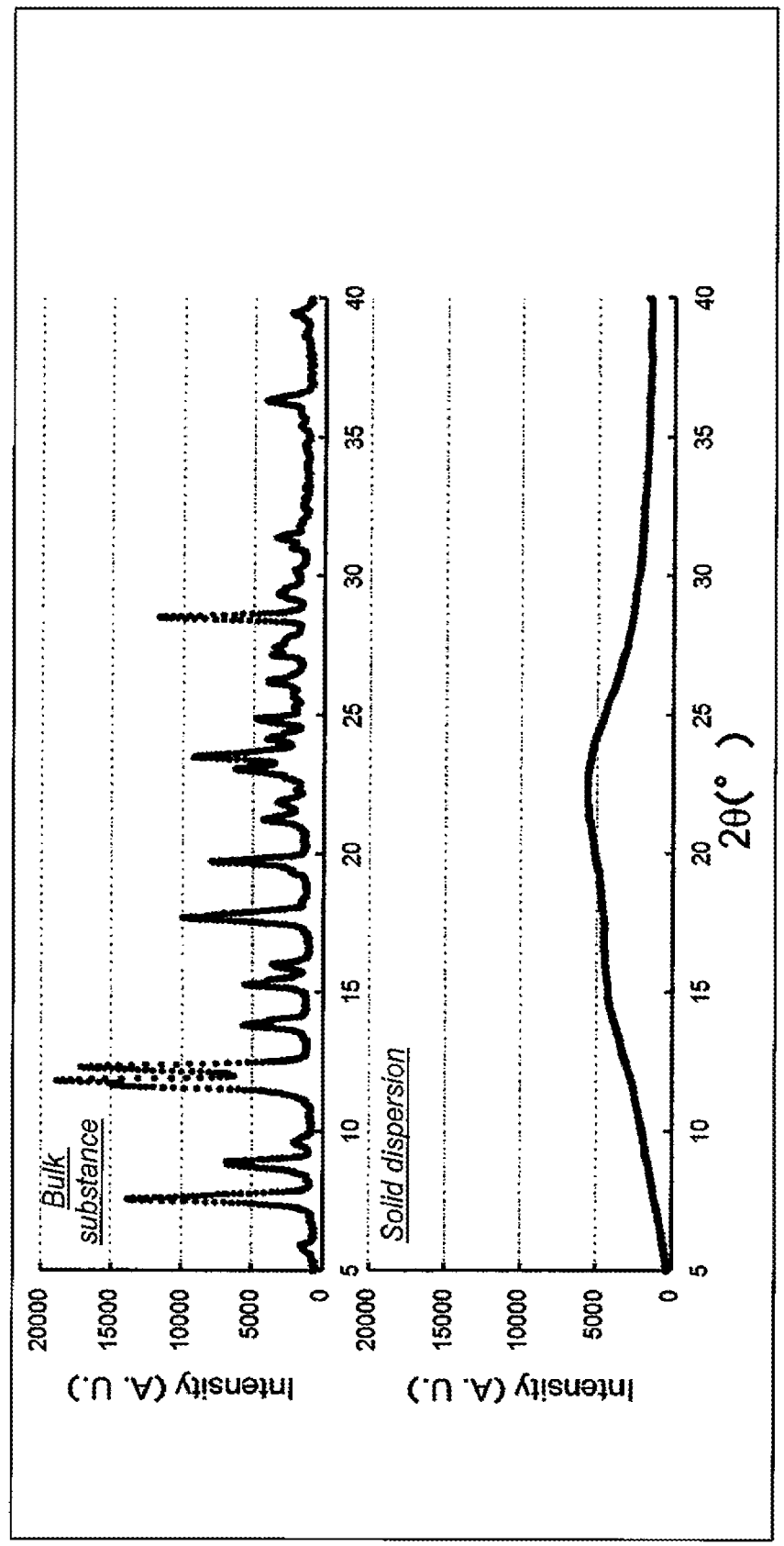
FIG. 1 is a diagram illustrating the results of nobiletin (upper graph) and nobiletin-methyl hesperidin solid dispersion (lower graph) according to Example 1 in powder X-ray diffraction.

The present invention relates to provision of a method for easily producing a nobiletin composition having high water solubility.

In consideration of the problems above, the present inventor found that a solid dispersion having amorphous nobiletin dispersed therein is obtained if nobiletin or a nobiletin-containing product is mixed with a water-soluble hesperidin derivative, is melted by heating, and is solidified by cooling, that the nobiletin in the solid dispersion has significantly high water solubility which is stably maintained in water, that the solid dispersion has high biological membrane permeability, and that the solid dispersion demonstrates high transferability into blood and transferability into tissues during oral administration to animals.

The present invention can provide a nobiletin-containing solid dispersion containing nobiletin having significantly improved water solubility. It is expected that use of the solid dispersion according to the present invention can improve the biological membrane permeability and transferability into blood and transferability into tissues of nobiletin during oral intake of the solid dispersion, can enhance the physiological function of nobiletin, and so on. In addition, the solid dispersion according to the present invention is suitable for use in food and beverage products because any organic solvent is not used in the production process.

The term used in the present invention "nobiletin" indicates 3',4',5,6,7,8-hexamethoxyflavone, which has the following structure:

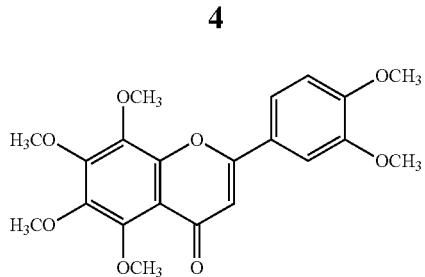

Nobiletin may be any selected from for example, those prepared through chemical synthesis, those separated from natural products, refined products of those prepared through chemical synthesis or separated from natural products, and commercially available products. Nobiletin may have any purity, for example, such that the solid dispersion of nobiletin can demonstrate a desired pharmacological effect. A "nobiletin-containing product" containing a high proportion or content of nobiletin can also be used. Such a nobiletin-containing product is prepared, for example, by extracting a fruit or pomace of citrus with an organic solvent having an ability to dissolve nobiletin, such as methanol or ethanol, and appropriately separating and refining the extract. Examples of the nobiletin-containing product include shequasar extracts containing nobiletin in a high content (such as "PMF90" <manufactured by Okinawa Research Center Co., Ltd., nobiletin proportion: more than about 60% by weight).

Examples of the "water-soluble hesperidin derivative" used in the present invention include hesperidins having water solubility improved through enzymatic or chemical treatment of hesperidin, such as transglycosylated hesperidins having a sugar moiety bonded to a sugar moiety (rutinose moiety) of hesperidin such as glucosyl hesperidin; and methyl hesperidin. Among these hesperidin derivatives, preferred are methyl hesperidin and glucosyl hesperidin from the viewpoint of water solubility.

As, known, "methyl hesperidin" includes mainly chalcone compounds (1) and flavanone compounds (2). Examples of the constitutional components of methyl hesperidin include those having the following structures:

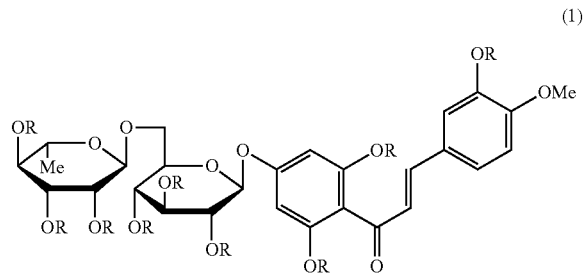

(1)

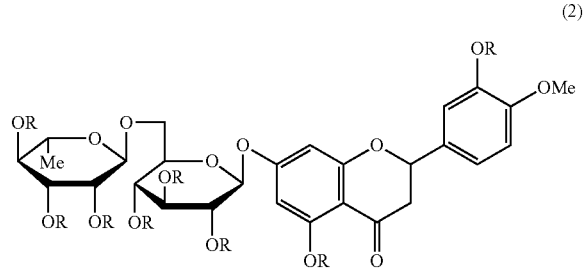

(2)

(where R represents a hydrogen atom or a methyl group).

Here, methyl hesperidin as a pharmaceutical additive and a food product additive is mainly handled as a mixture of compounds (3) and (4):

|  | R | Gl-2 | Rh-2 |
|---|---|---|---|
|  |  |  |  |

(3)

| (3-1) | Me | Me$_2$ | H |
| (3-2) | H | Me | H |
| (3-3) | H | H | H |

(4)

| (4-1) | H | Me | Me |
| (4-2) | H | Me | H |
| (4-3) | H | H | H |

(where Gl represents a glucose residue; Rh represents a rhamnose residue; Gl-2 represents a 2-position of the glucose residue (also includes a 3-position in the case of (3-1)); Rh-2 represents a 2-position of the rhamnose residue).

A cosmetic raw material, i.e., hesperidin methyl chalcone is handled as a compound represented by (5). A composition containing a large amount of chalcone compound is also referred to as hesperidin methyl chalcone.

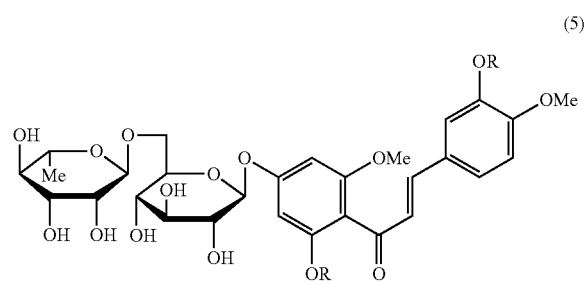

(5)

(where R represents a hydrogen atom or a methyl group).

The methyl hesperidin used in the present invention may contain both the chalcone compound (1) and the flavanone compound (2) listed above, or may contain only either of the chalcone compound (1) or the flavanone compound (2).

Examples of methyl hesperidin more suitable for the present invention include a mixture of the compound (3) and the compound (4).

Methyl hesperidin can be produced by a known method: For example, hesperidin is dissolved in an aqueous solution of sodium hydroxide, and the alkaline solution and a corresponding amount of dimethylsulfuric acid are acted. The reaction solution is neutralized with sulfuric acid, and is extracted with n-butyl alcohol, followed by removal of the solvent. The extract is recrystallized with isopropyl alcohol (Sakieki, Nihon Kagakuzasshi, 79, 733-6 (1958)). Any other production method can be used.

Commercially available methyl hesperidin-containing formulations may be used as methyl hesperidin. Examples thereof include "methyl hesperidin" (Tokyo Chemical Industry Co., Ltd.), "hesperidin methyl chalcone" (Sigma-Aldrich Corporation), "methyl hesperidin" (Hamari Chemicals, Ltd.), "methyl hesperidin" (Showa Denko K.K.), and "methyl hesperidin" (Alps Pharmaceutical Industry Co., Ltd.).

Examples of glucosyl hesperidin include monoglucosyl hesperidin ("αG hesperidin PA-T" (Toyo Sugar Refining Co., Ltd.), and "Hayashibara Hesperidin® S" (Hayashibara Co., Ltd.).

The nobiletin-containing solid dispersion according to the present invention can be produced through a step of mixing nobiletin or a nobiletin-containing product with a water-soluble hesperidin derivative, and then melting the mixture by heating, and a step of solidifying the melted product by cooling. As necessary, a variety of plasticizers and polymers can be added to nobiletin and the water-soluble hesperidin derivative before melting by heating.

Here, to increase the nobiletin content in the solid dispersion, the content of nobiletin in the mixture during mixing of nobiletin or a nobiletin-containing product with the water-soluble hesperidin derivative is preferably 1% by mass or more, more preferably 3% by mass or more, more preferably 4% by mass or more, more preferably 5% by mass or more, more preferably 7.5% by mass or more, more preferably 10% by mass or more, more preferably 15% by mass or more. Because of processability, the content is preferably 90% by mass or less, more preferably 70% by mass or less, more preferably 60% by mass or less, more preferably 50% by mass or less, more preferably 45% by mass or less, more preferably 40% by mass or less, more preferably 35% by mass or less. The content of nobiletin in the mixture is preferably from 1 to 90% by mass, more preferably from 3 to 70% by mass, more preferably from 4 to 60% by mass, more preferably from 5 to 50% by mass, more preferably from 7.5 to 45% by mass, more preferably from 10 to 40% by mass, more preferably from 15 to 35% by mass, particularly preferably 25%.

Although the content of the water-soluble hesperidin derivative varies according to the type thereof, the content in the mixture is preferably 10% by mass or more, more preferably 20% by mass or more, more preferably 25% by mass or more, more preferably 30% or more, more preferably 45% or more, more preferably 60% or more, more preferably 65% or more from the viewpoint of the solubility of nobiletin in water. To facilitate the preparation of the solid dispersion, the content is preferably 99% by mass or less, more preferably 97% by mass or less, more preferably 96% by mass or less, more preferably 92.5% or less, more preferably 90% or less, more preferably 85% or less. The content of methyl hesperidin in the mixture is from 10 to 99% by mass, more preferably from 20 to 97% by mass, more preferably from 25 to 96% by mass, more preferably from 30 to 92.5% by mass, more preferably from 45 to 90% by mass, more preferably from 60 to 85% by mass, more preferably from 65 to 85% by mass, particularly preferably 75%.

The mass ratio of nobiletin to the water-soluble hesperidin derivative [nobiletin/water-soluble hesperidin derivative] in the present invention during mixing of nobiletin or a nobiletin-containing product with the water-soluble hesperidin derivative is preferably 0.01 or more, more preferably 0.03 or more, still more preferably 0.04 or more, still more preferably 0.07 or more, still more preferably 0.1 or more to increase the content of the nobiletin in the resulting solid dispersion and facilitate the preparation of the solid dispersion. To increase the resulting solubility of nobiletin in water, the ratio is preferably 9 or less, more preferably 4 or less, more preferably 3 or less, more preferably 1 or less, more preferably 0.67 or less. The ratio is preferably from 0.01 to 9, more preferably from 0.03 to 4, more preferably from 0.04 to 3, still more preferably from 0.07 to 1, still more preferably from 0.1 to 0.67, particularly preferably 0.33.

The mixture of nobiletin or a nobiletin-containing product and the water-soluble hesperidin derivative can contain sugar or sugar alcohol as a plasticizer. Preferred examples thereof include glucose, fructose, maltose, mannose, rhamnose, ribose, xylose, trehalose, xylitol, mannitol, erythritol, arabinose, inositol, glucosamine, sucralose, and sorbitol.

The mixture of nobiletin or a nobiletin-containing product and the water-soluble hesperidin derivative can also contain a variety of polymers for the purposes of cost reduction, an improvement in dissolution behavior, and an improvement in physical properties of powder. Preferred examples thereof include polysaccharides and derivatives thereof and proteins such as linseed gum, arabic gum, arabinogalactan, welan gum, *cassia* gum, Bhatti gum, curdlan, carrageenan, xanthan gum, chitin, chitosan, guar gum, gellan gum, cyclodextrin, tamarind seed gum, tares gum, tragacanth gum, microcrystal cellulose, microfibrous cellulose, nisin, pullulan, pectin, macrbphomopsis gum, rhamsan gum, acetylated adipic acid-crosslinked starch, acetylated oxidized starch, acetylated phosphoric acid-crosslinked starch, alginic acid and salts thereof, starch sodium octenylsuccinate, casein and salts thereof, carboxymethyl cellulose and salts thereof, chondroitin sodium sulfate, hydroxypropylated phosphoric acid-crosslinked starch, hydroxypropyl cellulose, hydroxypropyl starch, hydroxypropyl methyl cellulose, methyl cellulose, phosphoric acid-crosslinked starch, and phosphorylated starch; and synthetic polymers such as sodium polyacrylate, polyvinylpyrrolidone, and polyvinylpolypyrrolidone.

Although the content of the plasticizer and the variety of polymers varies according to the types thereof, the content thereof in the mixture is preferably 5% by mass or more, more preferably 10% by mass or more, more preferably 15% by mass or more, more preferably 25% by mass or more in the view of the solubility of nobiletin, and is preferably 90% by mass or less, more preferably 85% by mass or less, more preferably 80% by mass or less, more preferably 70% by mass or less, more preferably 65% by mass or less, more preferably 50% by mass or less to facilitate the preparation of the solid dispersion. The content of the plasticizer and the variety of polymers in the mixture is preferably from 5 to 90% by mass, more preferably from 10 to 90% by mass, more preferably from 15 to 85% by mass, more preferably from 15 to 80% by mass, more preferably from 25 to 70% by mass, more preferably from 25 to 65% by mass, more preferably from 25 to 50% by mass.

The mass ratio of the plasticizer and the variety of polymer components to nobiletin [the plasticizer and the variety of polymers/nobiletin] during mixing of nobiletin or a nobiletin-containing product, the water-soluble hesperidin derivative, the plasticizer, and the variety of polymers is preferably 0.2 or more, more preferably 0.3 or more to facilitate the preparation of the solid dispersion. To increase the solubility of nobiletin in water, the mass ratio is preferably 19 or less, more preferably 17 or less, more preferably 9 or less, more preferably 6 or less, more preferably 2 or less. The mass ratio is preferably from 0.2 to 19, more preferably from 0.2 to 17, more preferably from 0.2 to 9, more preferably from 0.3 to 6, more preferably from 0.3 to 2.

The mass ratio of the plasticizer and the variety of polymers to the water-soluble hesperidin derivative [the plasticizer and the variety of polymers/water-soluble hesperidin derivative] during mixing of nobiletin or a nobiletin-containing product with the water-soluble hesperidin derivative and the plasticizer and the variety of polymers is 0.05 or more, 0.06 or more, more preferably 0.08 or more, still more preferably 0.11 or more to facilitate the preparation of the solid dispersion. The mass ratio is preferably 100 or less, 17 or less, more preferably 4 or less, still more preferably 2 or less to increase the solubility of nobiletin in water. The mass ratio is preferably from 0.05 to 100, more preferably from 0.05 to 17, more preferably from 0.08 to 4, more preferably from 0.11 to 2.

The mass ratio of nobiletin to the total amount of the water-soluble hesperidin derivative, the plasticizer, and the variety of polymers [nobiletin/(water-soluble hesperidin derivative the plasticizer and the variety of polymers)] during mixing of nobiletin or a nobiletin-containing product with the water-soluble hesperidin derivative and the plasticizer and the variety of polymers is preferably 0.01 or more, more preferably 0.02 or more, still more preferably 0.04 or more, still more preferably 0.07 or more, still more preferably 0.1 or more, still more preferably 0.17 or more, further still more preferably 0.25 or more to increase the content of nobiletin in the solid dispersion. The mass ratio is preferably 9 or less, more preferably 4 or less, still more preferably 3 or less, still more preferably 1 or less, still more preferably 0.67 or less, still more preferably 0.55 or less, still more preferably 0.43 or less to increase the resulting solubility of nobiletin in water. The mass ratio is preferably from 0.01 to 9, more preferably from 0.03 to 4, 0.04 to 3, still more preferably from 0.07 to 1, still more preferably from 0.1 to 0.67, still more preferably from 0.17 to 0.55, still more preferably from 0.25 to 0.43.

Although any known method of melting the mixture of nobiletin or a nobiletin-containing product with the water-soluble hesperidin derivative by heating can be used without particular limitation, melting by heating while the mixture is being stirred is preferred. For example, a kneader or an extruder such as an extruder or a kneader can be used. A stirrer such as a ribbon mixer can also be used. Examples thereof include an extruder manufactured by HAAKE, an extruder manufactured by Thermo Scientific, KZW134T manufactured by TECHNOVEL CORPORATION, a KRC kneader manufactured by Kurimoto, Ltd., Miracle K.C.K manufactured by ASADA IRON WORKS. CO., LTD., EA-20 manufactured by Suehiro EPM Corporation, and MC-1102 manufactured by N.P. & COMPANY INC. Examples of a heating method include steam and electricity.

Among these apparatuses, preferred is used of an extruder which included a screw and can simultaneously perform kneading and melting by heating, from the viewpoint of preparing a solid dispersion having a homogeneous composition. The extruder including a screw may be either a single screw type or a twin screw type. Preferred is a twin screw extruder to enhance the transportation ability. A preferred twin screw extruder is an extruder including a cylinder and two screws freely rotatably disposed therein. Twin screw extruders conventionally known can be used. The two screws may have the same rotational direction or the rotational direction opposite to each other. Preferred is the same rotational direction to enhance the transportation ability. The engagement of the screws in the extruder may be any one of a complete engagement, a partial engagement, and a non-engagement. Preferred are a complete engagement and a partial engagement to improve the processability.

The extruder including a screw preferably includes a so-called kneading disk unit in any portion of the screw to apply a strong compression shear force. The kneading disk unit includes a combination of several kneading disks disposed so as to be continuously shifted at a predetermined phase, such as 90 degrees. With the rotation of the screw, the kneading disk unit can force the mixture of nobiletin or a nobiletin-containing product and the water-soluble hesperidin derivative to pass through narrow gaps to apply a strong shear force to the mixture. In a preferred configuration of the screw, the kneading disk unit and a plurality of screw segments are alternately disposed. In the case of the twin screw extruder, two screws preferably have the same configuration.

A preferred method during use of the extruder including a screw is as follows: a mixture of nobiletin or a nobiletin-containing product and the water-soluble hesperidin derivative, preferably a roughly grounded product of the mixture is placed into the extruder, and is continuously processed by the rotation of the screw.

The number of rotations of the screw is preferably from 30 to 500 r/min, more preferably, from 50 to 300 r/min, still more preferably from 50 to 250 r/min, still more preferably from 80 to 200 r/min, particularly preferably 80 r/min.

The shear rate is preferably 10 $sec^{-1}$ or more, more preferably from 20 to 30,000 $sec^{-1}$, still more preferably from 50 to 3,000 $sec^{-1}$. A shear rate of 10 $sec^{-1}$ or more is preferred because of effective progress of pulverization.

The melted product melted in the extruder including a screw is extruded, and is molded.

Although a sufficient effect can be obtained through only one pass in the extruder, the number of passes through the extruder is preferably 2 passes or more to improve the dispersibility of nobiletin. The number of 1 to 10 passes is preferred from the viewpoint of productivity. Coarse particles can be pulverized through the repetition of passes, preparing a solid dispersion containing nobiletin having an even particle diameter. If 2 or more passes are performed, treatment may be performed by multiple extruders arranged in series in consideration of production ability.

The heating temperature is equal to or higher than the softening point of the water-soluble hesperidin derivative, preferably equal to or higher than the melting point of the water-soluble hesperidin derivative. The term "softening point" used in the present invention indicates a temperature at which a solid substance, when heated, softens and begins to deform. For example, methyl hesperidin has a softening point of 98° C., and glucosyl hesperidin has a melting point of 150° C. Methyl hesperidin softens or melts by heating, and nobiletin melts thereinto. Specifically, usually, methyl hesperidin has a melting point of 135° C.

The heating temperature in the present invention is preferably 95° C. or more, more preferably 100° C. or more, more preferably 105° C. or more. From the viewpoint of the thermal stability of nobiletin, the heating temperature is preferably 200° C. or less, more preferably 185° C. or less, more preferably 180° C. or less, more preferably 160° C. or less, more preferably 140° C. or less. The heating temperature is preferably from 95 to 200° C., more preferably from 95 to 180° C., more preferably from 100 to 185° C., more preferably from 100 to 160° C., more preferably from 105 to 140° C., particularly preferably 130° C.

From the viewpoint of the thermal stability of the water-soluble hesperidin derivative and nobiletin and the productivity, the heating time is preferably 30 minutes or less, more preferably 15 minutes or less, more preferably 10 minutes or less from the point of time when the temperature reaches the melting temperature of the water-soluble hesperidin derivative. From the viewpoint of the mixing of the water-soluble hesperidin derivative with nobiletin and the solubility of nobiletin in water, the heating time is preferably 1 minute or more, more preferably 3 minutes or more, more preferably 5 minutes or more. The heating time is preferably from 1 to 30 minutes, more preferably from 3 to 15 minutes, more preferably from 5 to 10 minutes, particularly preferably 10 minutes from the point of time when the temperature reaches the melting temperature of the water-soluble hesperidin derivative.

The melted product is then cooled to be solidified. This treatment converts nobiletin into an amorphous state, preparing a solid dispersion containing nobiletin in an amorphous state.

The term "amorphous" indicates that the molecular arrangement has no certain regularity. The amorphous (amorphous) state can be verified by powder X-ray diffraction.

Nobiletin contained in the solid dispersion according to the present invention has a degree of crystallization of preferably 50% or less, more preferably of 40% or less, more preferably of 20% or less, more preferably of 10% or less, more preferably of 5% or less. Particularly preferably, nobiletin contained in the solid dispersion has a degree of crystallization of 0%, that is, is completely amorphous.

The solid dispersion according to the present invention preferably has no crystalline diffraction peak of nobiletin detected in the measurement by powder X-ray diffraction.

The degree of crystallization of nobiletin can be calculated by the following method. First, from the diffraction intensity values by X-ray diffraction, peaks are separated into a crystallinity diffraction line and an amorphous halo by a profile fitting method without considering influences such as incoherent scattering and lattice disorder. In the next step, the degree of crystallization of nobiletin determined from the integrated intensity of the peaks is calculated from the following calculation expression [1]:

$$\text{Degree of crystallization (\%) of nobiletin} = [\Sigma I\alpha(\Sigma I\alpha + \Sigma Iam)] \times 100 \quad [1]$$

[where $\Sigma I\alpha$ represents the sum of the integrated intensities of the peaks of the crystallinity diffraction line, and $\Sigma Iam$ represents the sum of the integrated intensities of the peaks of the diffraction line of the amorphous moiety]

A preferred temperature of a coolant during cooling of the melted product is lower than the melting temperature of the water-soluble hesperidin derivative, preferably 50° C. or less, more preferably 30° C. or less. A cooling method is, for example, to place the solid dispersion under an atmosphere at preferably 50° C. or less, more preferably 30° C. or less, more preferably room temperature (25° C.). Preferred is quenching by blowing cool air to the solid dispersion after the heat treatment. The cooling rate of the solid dispersion calculated from the time taken to cool the solid dispersion from the temperature for the heat treatment to 50° C. is preferably 0.1° C./s or more, more preferably 0.2° C./s or more, more preferably 0.3° C./s or more. From the viewpoint of the restrictions on the facility for production and the like, the cooling rate is, for example, 100° C./s or less, more preferably 50° C./s or less. The cooling time is preferably 30 minutes or less, more preferably 20 minutes or less, more preferably 10 minutes or less, more preferably 5 minutes or less.

The solid dispersion containing nobiletin and the water-soluble hesperidin derivative solidified by cooling can be molded into any shape and any size. Examples thereof include pellet shapes, and granular shapes. Furthermore, the solid dispersion may be pulverized when necessary.

The solid dispersion containing nobiletin ("nobiletin-containing solid dispersion") according to the present invention thus prepared has significantly high water solubility (initial solubility, solubility over time).

Figure 22:
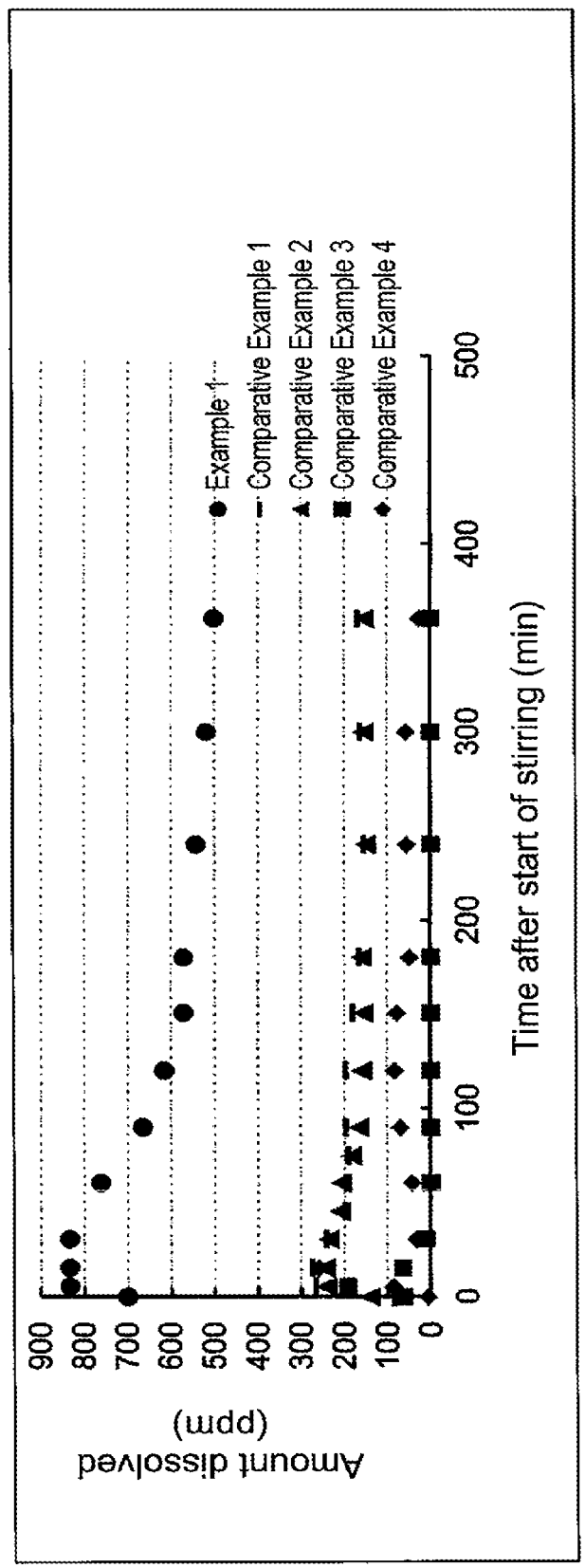
FIG. 22 is a diagram illustrating the results of the follow-up over time of the solubility using several examples of solid dispersion.

For example, as shown in Examples described later, solubility over time of nobiletin (for example, dissolved nobiletin concentration when the nobiletin-containing solid dispersion is added to water, and is stirred for 6 hours (the area under the curve up to 6 hours from the start of stirring (the abscissa: time (unit=minutes), the ordinate: dissolved concentration (unit=ppm)) is significantly high, for example, about $2.20 \times 10^5$ ppm·min, and a high dissolved concentration is maintained for a long time (see FIG. 22). Such a high solubility is an unexpected effect which is not exhibited in solid dispersions prepared by mixing a compound known as a polyphenol having poor solubility similar to that of nobiletin (such as hesperidin, sesamin, or ellagic acid) with a water-soluble hesperidin derivative.

The nobiletin-containing solid dispersion according to the present invention also has significantly high permeability of nobiletin to cell membranes derived from human small-intestinal epithelial cells. The effect is also unexpected from the solid dispersions of other poorly soluble polyphenols.

The content of water in the solid dispersion is preferably 20% by mass or less, more preferably 10% by mass or less, more preferably 7% by mass or less, more preferably 5% by mass or less to prepare fine products and provide favorable handling properties.

The solid dispersion containing nobiletin obtained by the production method according to the present invention can be used in a variety of food and beverage products, pharmaceuticals, quasi-drugs, cosmetics, and the like. Especially, the solid dispersion containing nobiletin is useful in applications to aqueous products.

Examples of the food and beverage products include beverages, breads, noodles, sweets such as cookies, snacks, jellies, dairy products, frozen food products, ready-to-eat food products such as powder coffee, starch processed products, processed meat products, other processed food products, seasonings, and liquid, solid, or semi-solid food and beverage products such as nutritional supplement products. Examples of the pharmaceuticals or the quasi-drugs include dosage forms, such as tablets (such as chewable tablets), capsules, and powders. Examples of the cosmetics include cleansers, skin lotions, makeup cosmetics, sunscreen cosmetics, acne cosmetics, deodorant cosmetics, whitening cosmetics, shampoos, and hair growers.

Aspects and preferred embodiments according to the present invention will be shown below:

<1> A method for producing a solid dispersion comprising nobiletin, comprising the step of mixing nobiletin or a nobiletin-containing product with a water-soluble hesperidin derivative, and then melting the mixture by heating; and the step of solidifying the melted product by cooling.

<2> In <1>, the content of nobiletin in the mixture of nobiletin or a nobiletin-containing product and the water-soluble hesperidin derivative is preferably 1% by mass or more, more preferably 3% by mass or more, more preferably 4% by mass or more, more preferably 7.5% by mass or more, more preferably 10% by mass or more, more preferably 15% by mass or more, preferably 90% by mass or less, more preferably 80% by mass or less, more preferably 75% by mass or less, more preferably 50% by mass or less, more preferably 40% by mass or less, more preferably 35% by mass or less. The content is preferably from 1 to 90% by mass, more preferably from 3 to 80% by mass, more preferably from 4 to 75% by mass, more preferably from 7.5 to 50% by mass, more preferably from 10 to 40%, more preferably from 15 to 35%, particularly preferably 25%.

<3> In <1> or <2>, the content of the water-soluble hesperidin derivative in the mixture of nobiletin or a nobiletin-containing product and the water-soluble hesperidin derivative is preferably 10% by mass or more, more preferably 20% by mass or more, more preferably 25% by mass or more, more preferably 30% or more, more preferably 45% or more, more preferably 60% or more, more preferably 65% or more, preferably 99% by mass or less, more preferably 97% by mass or less, more preferably 96% by mass or less, more preferably 92.5% or less, more preferably 90% or less, more preferably 85% or less. The content is preferably from 10 to 99% by mass, more preferably from 20 to 97% by mass, more preferably from 25 to 96% by mass, more preferably from 30 to 92.5% by mass, more preferably from 45 to 90% by mass, more preferably from 60 to 85% by mass, more preferably from 65 to 85% by mass, particularly preferably 75% by mass.

<4> In <1> to <3>, the mass ratio of nobiletin to the water-soluble hesperidin derivative [nobiletin/water-soluble hesperidin derivative] during mixing of nobiletin or a nobiletin-containing product with the water-soluble hesperidin derivative is preferably 0.01 or more, more preferably 0.03 or more, more preferably 0.04 or more, more preferably 0.07 or more, more preferably 0.1 or more, and preferably 9 or less, more preferably 4 or less, more preferably 3 or less, more preferably 1 or less, more preferably 0.67 or less. The mass ratio is preferably from 0.01 to 9, more preferably from 0.03 to 4, more preferably from 0.04 to 3, more preferably from 0.07 to 1, more preferably from 0.1 to 0.67, particularly preferably 0.33.

<5> A method for producing the solid dispersion according to any one of <1> to <4>, comprising the step of mixing nobiletin or a nobiletin-containing product with a water-soluble hesperidin derivative, and then melting the mixture by heating, wherein the step is performed using an extruder including a screw.

<6> The method for producing the solid dispersion according to <5>, wherein the extruder including a screw is preferably a single screw extruder or a twin screw extruder, more preferably a twin screw extruder, more preferably a twin screw extruder including two screws freely rotatably disposed inside a cylinder thereof.

<7> The method for producing a solid dispersion according to <5> or <6>, wherein the number of rotations of the screw is preferably from 30 to 500 r/min, more preferably from 50 to 300 r/min, more preferably from 50 to 250 r/min, more preferably from 80 to 200 r/min, particularly preferably 80 r/min.

<8> The method for producing the solid dispersion according to any one of <5> to <7>, wherein the shear rate is preferably 10 $sec^{-1}$ or more, more preferably from 20 to 30,000 $sec^{-1}$, more preferably from 50 to 3,000 sec-1.

<9> In <1> to <8>, the heating temperature is preferably 95° C. or more, more preferably 100° C. or more, more preferably 105° C. or more, preferably 200° C. or less, more preferably 185° C. or less, more preferably 180° C. or less, more preferably 160° C. or less, more preferably 140° C. or less. The heating temperature is preferably 95 to 200° C., more preferably 95 to 180° C., more preferably 100 to 185° C., more preferably 100 to 160° C., more preferably 105 to 140° C., particularly preferably 130° C.

<10> In <1> to <9>, the heating time is preferably 30 minutes or less, more preferably 15 minutes or less, more preferably 10 minutes or less, more preferably 1 minute or more, more preferably 3 minutes or more, more preferably 5 minutes or more from the point of time when the temperature reaches the melting temperature of the water-soluble hesperidin derivative. The heating time is preferably from 1 to 30 minutes, more preferably from 3 to 15 minutes, more preferably from 5 to 10 minutes, particularly preferably 10 minutes from the point of time when the temperature reaches the melting temperature of the water-soluble hesperidin derivative.

<11> The method for producing the solid dispersion according to any one of <1> to <10>, wherein nobiletin has a degree of crystallization of preferably 50% or less, more preferably 40% or less, more preferably 20% or less, more preferably 10% or less, more preferably 5% or less, and particularly preferably 0%.

<12> The method for producing the solid dispersion according to any one of <1> to <11>, wherein the cooling temperature is preferably a temperature lower than the melting temperature of the water-soluble hesperidin derivative, more preferably 50° C. or less, more preferably 30° C. or less, and more preferably under an atmosphere at room temperature (25° C.)

<13> The method for producing the solid dispersion according to any one of <1> to <12>, wherein the cooling rate of the solid dispersion calculated form the time taken to cool the solid dispersion from the heat treatment temperature to 25° C. is preferably 0.1° C./s or more, more preferably 0.2° C./s or more, more preferably 0.3° C./s or more, and preferably 100° C./s or less, more preferably 50° C./s or less.

<14> The method for producing the solid dispersion according to any one of <1> to <13>, wherein the cooling time is preferably 30 minutes or less, more preferably 20 minutes or less, more preferably 10 minutes or less, and more preferably 5 minutes or less.

<15> The method for producing the solid dispersion according to any one of <1> to <14>, wherein the water content in the solid dispersion is preferably 20% by mass or less, more preferably 10% by mass or less, more preferably 7% by mass or less, and more preferably 5% by mass or less.

<16> The method for producing the solid dispersion according to any one of <1> to <15>, wherein the water-soluble hesperidin derivative is methyl hesperidin.

<17> A nobiletin-containing solid dispersion comprising nobiletin or a nobiletin-containing product, and a water-soluble hesperidin derivative, wherein nobiletin having a degree of crystallization of 10% or less as calculated from an X-ray diffraction spectrum is dispersed.

<18> A nobiletin-containing solid dispersion comprising nobiletin or a nobiletin-containing product, and a water-soluble hesperidin derivative, wherein nobiletin is dispersed and has a degree of crystallization of 10% or less as calculated from an X-ray diffraction spectrum.

<19> The nobiletin-containing solid dispersion according to <17> or <18>, wherein the water-soluble hesperidin derivative is methyl hesperidin.

<20> A nobiletin-containing solid dispersion obtained by the method according to any one of <1> to <16>, wherein nobiletin has a degree of crystallization of 10% or less as calculated from an X-ray diffraction spectrum.

<21> A food or beverage product, a pharmaceutical, or a quasi-drug comprising the nobiletin-containing solid dispersion according to any one of <17> to <20>.

EXAMPLES

[Quantitation of Poorly Water-Soluble Substance]

Quantitation of poorly water-soluble polyphenols was performed at a column temperature of 40° C. by a gradient method using a high performance liquid chromatograph manufactured by Agilent Technologies, Inc., to which a column L-Column ODS-2 (4.6 mm$\phi$×50 mm, 2 μm) manufactured by Chemicals Evaluation and Research Institute, Japan was attached.

The amount of a sample injected was 10 μL, a mobile phase Solution A was a 0.1% by weight aqueous solution of trifluoroacetic acid, and a mobile phase Solution B was acetonitrile. The flow rate was 1.0 mL/min. The gradient conditions are shown below.

| Time (minutes) | Solution A (%) | Solution B (%) |
|---|---|---|
| 0 | 99 | 1 |
| 1 | 99 | 1 |
| 4 | 5 | 95 |
| 5 | 5 | 95 |
| 5.01 | 99 | 1 |
| 6 | 99 | 1 |

Quantitation of nobiletin, ellagic acid, hesperidin, and sesamin was performed through the detection of the absorbances of nobiletin at a wavelength of 320 nm, ellagic acid at a wavelength of 254 nm, and hesperidin and sesamin at a wavelength of 280 nm.

[Refining Method of Monoglucosyl Hesperidin (mGHes)]

mGHes was refined at a column temperature of 40° C. by an isocratic method using a high performance liquid preparative chromatograph manufactured by GL Sciences Inc., to which a column Inertsil ODS-3 (14 mm$\phi$×250 mm, 5 μm) manufactured by GL Sciences Inc. was attached.

The preparative sample used was an aqueous solution of 20 w/v % αG hesperidin PA-T (manufactured by Toyo Sugar Refining Co., Ltd.), and the amount of a sample injected per one preparative operation was 250 μL. The mobile phase was a mixed solution of Solution A and Solution B (A:B=25:75). Solution A was a 0.1% by weight aqueous solution of trifluoroacetic acid, Solution B was acetonitrile. The flow rate was at 15.0 mL/min. An absorbance at a wavelength of 280 nm was used in the detection.

The mGHes-containing solution obtained by this method was condensed under reduced pressure to remove acetonitrile. The condensed solution was refined by column chromatography using DIAION HP-20 (resin manufactured by Mitsubishi Chemical Corporation). The refined product was condensed under reduced pressure, and was freeze dried to prepare mGHes as powder. This product was used as a raw material for a solid dispersion.

[X-Ray Diffraction Analysis]

The intensity of X-ray diffraction was measured using "MiniFlexII" manufactured by Rigaku Corporation under the following conditions: X-ray source: Cu/Kα-radiation, tube voltage: 30 kV, tube current: 15 mA, range for measurement: diffraction angle: 5 to 40°, and X-ray scan speed:

10°/min. A sample for measurement was prepared by compressing pellets having an area of 400 mm² and a thickness of 0.5 mm.

[Evaluation of Solubility Over Time]

30 mL of deionized water was placed into a 50-mL screw cap tube (manufactured by Maruemu Corporation, No. 2, brown), and 100 mg of a solid dispersion (containing 25 mg of a poorly water-soluble substance) was added, followed by stirring at 500 rpm using a 2 cm stirrer chip. Part of the sample was filtered through a 0.45 µm cellulose acetate filter from the start of the stirring at 0 minutes to 6 hours of stirring to determine the amount of nobiletin dissolved by the method described in [Quantitation of poorly water-soluble substance] described above.

[Evaluation of Caco-2 Cells Membrane Permeability]

Test Example 1: Permeability Promotion Test of Bulk Substance of Poorly Water-Soluble Substance and its Solid Dispersion to Small Intestine Epithelia Using Human Colorectal Cancer-Derived Epithelial Cells Caco-2 cells (human colorectal cancer-derived epithelial cells, available from DS Pharma Biomedical Co., Ltd.) were cultured at 37° C. in the presence of 5% $CO_2$. The culture was performed using a Caco-2 cell differentiation culture medium set (manufactured by Corning Incorporated), and a BioCoat Fibrillar Collagen HTS multiwell insert (24 wells, membrane pore: 1 µm, manufactured by Corning Incorporated). Caco-2 cells were suspended in a basal seeding culture medium containing MITO+™ Serum Extender, and were seeded in the upper portion (top membrane) of the insert. The same culture medium was added to the lower portion (bottom membrane) of the insert. After the culturing of Caco-2 cells for 24 hours, the basal seeding culture medium was replaced with an Entero-STIM intestine epithelia differentiation culture medium containing MITO+™ Serum Extender. Subsequently, the cells were cultured for another 48 hours to differentiate into sheets of small intestine epithelial cells.

To verify the formation of the tight junction of the intestinal tract, the transepithelial electric resistance (TEER) value was measured using a Millicell ERS (manufactured by Millipore Corporation) immediately before the permeability promotion test of the bulk substance of the poorly water-soluble substance and its solid dispersion to the small intestine epithelia, and Caco-2 cells having a TEER having a predetermined value (350 $\Omega \cdot cm^2$) or more were used.

A sample for evaluation was prepared as follows. 6 mL of HESS (manufactured by Invitrogen Corporation, 10 mM MES, 5 mM glucose, 10 mM glutamine, and 1 mM ascorbic acid were added thereto to adjust the pH to 6.0) was placed into a 20 mL screw cap tube (manufactured by Maruemu Corporation, No. 2, brown). The bulk substance (10 mg) of the poorly water-soluble substance or its solid dispersion (40 mg) (containing 10 mg of the poorly water-soluble substance) was added, followed by stirring at 300 rpm for 10 minutes using a 2 cm stirrer chip. After the stirring, the solution filtered through a 0.45 µm cellulose acetate filter and its diluted solution were used as samples for evaluation. Table 1 shows the results of evaluation of a 30-fold diluted solution of this filtrate with HBSS, the diluted solution being placed into the upper portion of the insert.

After cell sorting by the measurement of TEER, the upper portion and lower portion of the insert were purged with HBSS to wash the insert two times. Subsequently, an aqueous solution of the poorly water-soluble substance and the solid dispersion prepared by the method described above or its diluted solution was placed into the upper portion of the insert. The evaluated concentrations of extracts are shown in Table 2. HBSS (10 mM HEPES, 5 mM glucose, 10 mM glutamine, pH: 7.4) was placed into the lower portion of the insert. Caco-2 cells were then cultured at 37° C. for 4 hours in the presence of 5% $CO_2$.

Subsequently, HBSS in the lower portion of the insert was recovered, and quantitation of the poorly water-soluble substance which passed through the small intestine epithelia was performed by liquid chromatograph-tandem mass spectrometry (LC-MS/MS) according to the following method.

[LC Conditions]

Using a high performance liquid chromatograph manufactured by Agilent Technologies, Inc., a column L-Column ODS-2 (4.6 mm×50 mm, 2 µm) manufactured by Chemicals Evaluation and Research Institute, Japan was attached thereto. The measurement was performed by a gradient method at a column temperature of 40° C.

In the measurement of nobiletin, sesamin, and hesperidin, the amount of the sample injected was 10 µL, a mobile phase Solution A was a 0.1% by weight aqueous solution of formic acid, and Solution B was acetonitrile. The flow rate was 0.6 mL/min. The gradient condition is shown as follows:

| Time (minutes) | Solution A (%) | Solution B (%) |
|---|---|---|
| 0 | 90 | 10 |
| 0.5 | 90 | 10 |
| 4 | 10 | 90 |
| 5 | 10 | 90 |
| 5.01 | 90 | 10 |
| 6 | 90 | 10 |

In the measurement of ellagic acid, the amount of the sample injected was 10 µL, a mobile phase Solution A was a 5.0% by weight aqueous solution of formic acid, and Solution B was acetonitrile. The flow rate was 0.6 L/min. The gradient condition is shown as follows:

| Time (minutes) | Solution A (%) | Solution B (%) |
|---|---|---|
| 0 | 99 | 1 |
| 0.5 | 99 | 1 |
| 4 | 5 | 95 |
| 5 | 5 | 95 |
| 5.01 | 99 | 1 |
| 6 | 99 | 1 |

[MS/MS Conditions]

The mass spectrometer used was QTRAP®4500 (manufactured by AB Sciex LLC). The measurement was performed as follows: the scan condition: MRM, parameter table: analyte. The quantitation was performed by detecting ions at MRM (m/Z) 404.0→374.0 in nobiletin in the positive ion mode, ions at MRM (m/Z) 355→276.9 in sesamin in the positive ion mode, ions at MRM (m/Z) 611.2→71.0 in hesperidin in the positive ion mode, and ions at MRM (m/Z) 300.9→284.0 in ellagic acid in the negative mode.

[Evaluation of Cell Survival Rate by LDH Activity Measurement Test]

Test Example 2: LDH Activity Measurement Test

HBSS in the upper portion of the insert in Test Example 1 was recovered. According to the method described below, the cytotoxicity of each evaluation sample was determined from the measurement of the activity of LDH (Lactate dehydrogenase) in the solution released from the Caco-2 cells forming the cell membrane. The cytotoxicity was used to evaluate the cell survival rate of each sample.

The cytotoxicity was evaluated using LDH Cytotoxicity Assay Kit (manufactured by Cayman Chemical Company) by a predetermined method. The test solution in the upper portion of the insert after the end of the evaluation was used as a sample, and the LDH activity was calculated from the amount of formazan produced by LDH contained (quantitatively determined from the absorbance intensity at 490 nm). The cell survival rate was calculated where the LDH activity of the test solution in the upper portion of the insert after the end of the evaluation when the 1.0% Triton X-100 HBSS solution was used as a sample for Caco-2 cells membrane permeability evaluation (Test Example 1) corresponded to a survival rate of 0%. From the following expression, a rate of variation in LDH activity was calculated. (Expression for calculation) cell survival rate (%)= ((LDH activity of test solution in upper portion of insert after end of evaluation of 1.0% Triton×HBSS solution)−(LDH activity of test solution in upper portion of insert after end of evaluation of sample))/(LDH activity of test solution in upper portion of insert after end of evaluation of 1.0% Triton×HBSS solution)

The average of the cell survival rates determined from Expression for calculation and the standard error (N=3-4) are shown in Table 1-1.
[Evaluation of Transferability of Nobiletin into Blood Circulation During Oral Administration to Mice]
(Animals)

C57BL/6J mice (male, 6 week-old) were purchased from CLEA Japan, Inc. The mice were habituated to the environment for one week or more, and were fed to a test. Each of the test groups consisted of 8 mice, which was believed to be the minimum number required to ensure the statistical significance of the test system. (Preparation of test solution) In the test, a nobiletin bulk substance, a nobiletin-methyl hesperidin mixture (composition in Comparative Example 5), and nobiletin-methyl hesperidin (composition in Example 1) were used as samples administrated. Using the nobiletin bulk substance, the composition in Comparative Example 5, or the composition in Example 1, an aqueous solution or aqueous suspension containing 20 mg/mL nobiletin was prepared.
(Oral Administration and Preparation of Plasma)

Mice were bred in the facility for one week under ad libitum feeding of solid food (CE-s), and the test was performed using the mice. The mice were fasted for 16 hours, and blood was initially collected from the orbital sinus of each mouse under isoflurane anesthesia (heparin-treated micro hematocrit blood collection tube, manufactured by VITREX Medical A/S). Each sample solution was then administrated into the stomach of the mice at a dose of 200 mg/kg weight per mouse using a probe. After the administration of the solution, blood was collected from the orbital sinus of each mouse under isoflurane anesthesia after 10, 30, 60, 90, and 120 minutes.

The collected blood samples were centrifuged at 12,000 rpm for 10 minutes, and 30 µL of plasma in each sample was recovered into an Eppendorf tube. The recovered plasmas were stored at −80° C. until the measurement of the nobiletin content. The nobiletin concentration in the plasma was measured by LC-MS/MS.
(Treatment of Plasma Sample)

30 µL of acetonitrile was added to 30 µL of the recovered plasma, was stirred with a vortex mixer for 5 seconds, and was centrifuged at 12,000 rpm for 15 minutes at room temperature. 30 µL of the resulting supernatant was recovered in a vial for LC measurement, 30 µL of acetonitrile was further added, and was mixed with a vortex mixer. The nobiletin concentration was then measured by LC-MS/MS.
[Evaluation of Transferability of Nobiletin into Tissues During Oral Administration to Mice]
(Animals)

C57BL/6J mice (male, 6 week-old) were purchased from CLEA Japan, Inc. The mice were habituated to the environment for one week or more, and were fed to a test. Each of the test groups consisted of 5 mice, which was believed to be the minimum number required to ensure the statistical significance of the test system.
(Preparation of Test Solution)

The test used three samples for administration, that is, a nobiletin bulk substance, a nobiletin-methyl hesperidin mixture (composition in Comparative Example 5), and nobiletin-methyl hesperidin (composition in Example 1). Using the nobiletin bulk substance, the composition in Comparative Example 5, or the composition in Example 1, an aqueous solution or aqueous suspension containing 15 mg/mL nobiletin was prepared.
(Oral Administration and Preparation of Plasma)

Mice were bred in the facility for one week under ad libitum feeding of solid food (CE-s), and the test was performed using the mice. The mice were fasted for 16 hours, and each sample solution was administrated into the stomach of the mice under isoflurane anesthesia at a dose of 50 mg/kg weight per mice using a probe. After 30 minutes of the administration of the solution, whole blood was collected from the abdominal large vein under isoflurane anesthesia. The mice were euthanized. The blood collection was performed using a heparin-treated micro hematocrit blood collection tube, manufactured by VITREX Medical A/S.

Subsequently, blood was removed from all the tissues under perfusion to collect tissues (liver, white adipose tissue, brown adipose tissue, gastrocnemius, soleus muscle, shin bone, thighbone, and portions of left and right brains (brain cortex, hippocampus)). The collected blood samples were centrifuged at 12,000 rpm for 10 minutes, and 30 µL of plasma in each sample was recovered into an Eppendorf tube. The plasmas and the tissue samples obtained were stored at −80° C. until the measurement of the nobiletin content.
(Treatment of Tissue Samples Other than Bone Tissues)

300 µL of acetonitrile was added to 10 mg of the recovered tissues, was stirred for 3 minutes with a homogenizer (Physcotron NS-310E (manufactured by MICROTEC CO., LTD.)), and then was centrifuged at 4° C. and 15,000 rpm for 20 minutes. 50 µL of the supernatant obtained was recovered in a vial for LC measurement, and the nobiletin concentration was measured by LC-MS/MS.
(Treatment of Bone Tissue Samples)

10 mg of the recovered bone tissues were cut with a pair of dissecting scissors, and the blood was removed through centrifugation at room temperature and 10,000 rpm for 1 minute. The sample was frozen with liquid nitrogen, and was crushed with a crusher (Cryo-Press CP-100W (manufactured by MICROTEC CO., LTD.)). 300 µL of acetonitrile was added to perform an ultrasonic treatment (ultrasonic washer FU-9H (manufactured by Tokyo Garasu Kikai, K.K.)) for 15 minutes. 50 µL of the supernatant obtained was recovered in a vial for LC measurement, and the nobiletin concentration was measured by LC-MS/MS.

Example 1

Nobiletin (manufactured by Wako Pure Chemical Industries, Ltd.) and methyl hesperidin (manufactured by Tokyo Chemical Industry Co., Ltd.) were mixed in the proportion of 25% by mass and 75% by mass, respectively. The mixture was treaded using a twin screw extruder (manufactured by HAAKE) on the following condition: the heating temperature: 160° C., the heating time: 10 minutes, and the number of rotations of the screw: 80 r/min. The mixture was cooled to 25° C. (cooling rate: 0.52° C./s) in 5 minutes by blowing cool air at 25° C., preparing a solid dispersion. At this time, the inside of the extruder had no clogging, and the molded body of the solid dispersion was preferably discharged. The powder X-ray diffraction of the solid dispersion is shown in FIG. 1. From the loss of the diffraction peak derived from nobiletin, it was verified that nobiletin became amorphous in the solid dispersion. The degree of crystallization of the solid dispersion was estimated to be 0%. Because methyl hesperidin has no peak in X-ray diffraction, it is estimated that nobiletin has a degree of crystallization of 0%.

Figure 6:
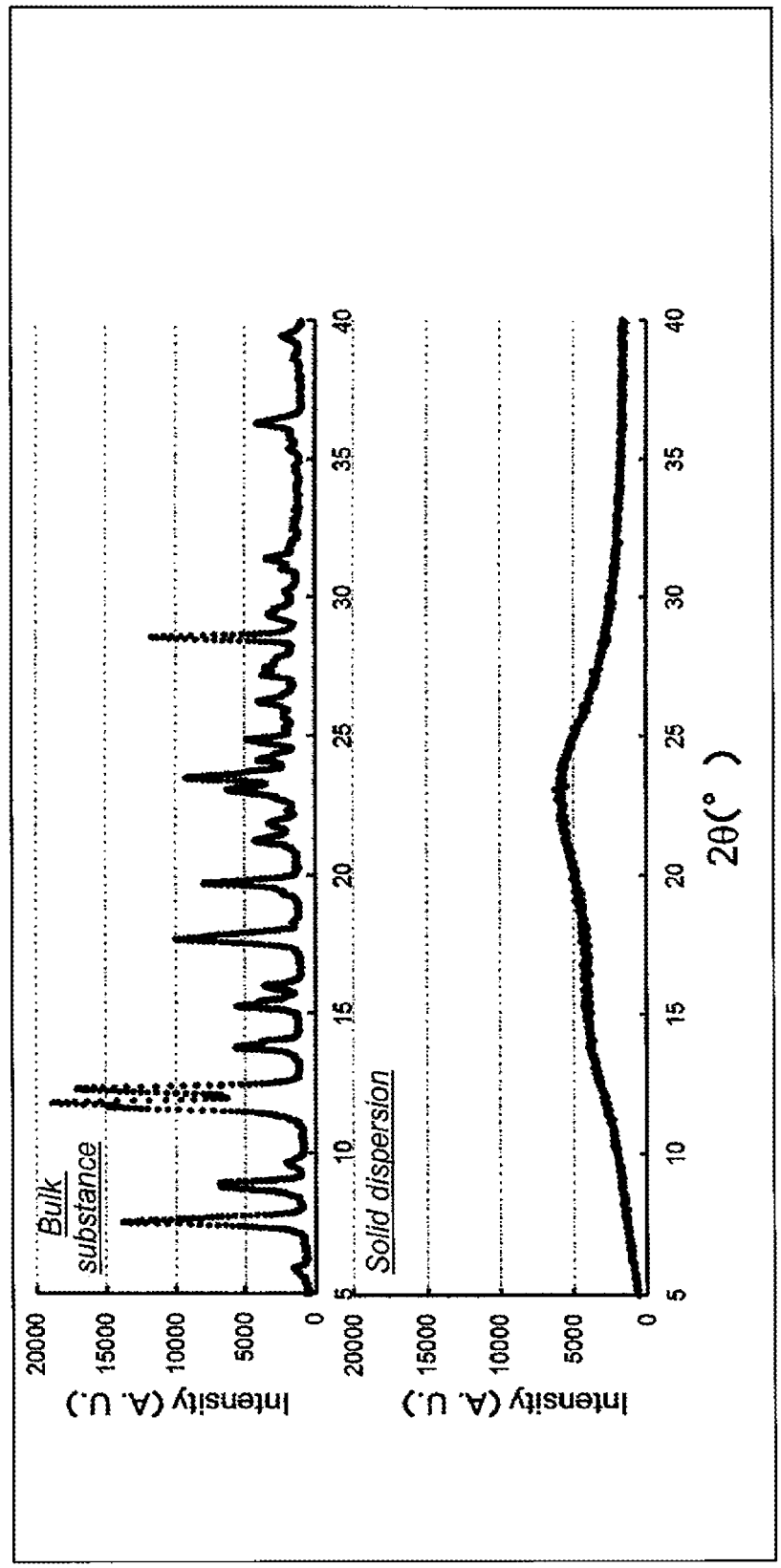
FIG. 6 is a diagram illustrating the results of nobiletin (upper graph) and nobiletin-methyl hesperidin solid dispersion (lower graph) according to Example 6 in powder X-ray diffraction.

The concentration of nobiletin dissolved in the solid dispersion was measured according to [Evaluation of solubility over time]. The result shows that the area under the curve until 6 hours from the start of stirring (the abscissa: time (unit=minutes), the ordinate: concentration of nobiletin dissolved (unit=ppm)) was $2.20 \times 10^5$ ppm·min, and a significantly high concentration of nobiletin dissolved was maintained for a long time (FIG. 6 and Table 1-1).

The nobiletin concentration was 132 µM when the evaluation of the upper portion of the insert was started in the solid dispersion test according to [Evaluation of Caco-2 cells membrane permeability], and was 4.33 µM at the end of the evaluation of the lower portion of the insert. From these results, such high solubility improved the amount of nobiletin permeating the membrane (Table 1-1).

Example 2

Nobiletin (manufactured by Wako Pure Chemical Industries, Ltd.) as a poorly water-soluble substance and methyl hesperidin (manufactured by Tokyo Chemical Industry Co., Ltd.) were mixed in a proportion of 10% by mass and 90% by mass, respectively. Using this mixture, a solid dispersion was prepared in the same manner as in Example 1 (heating temperature: 160° C., heating time: 10 minutes, and the number of rotations of the screw: 80 r/min).

Figure 2:
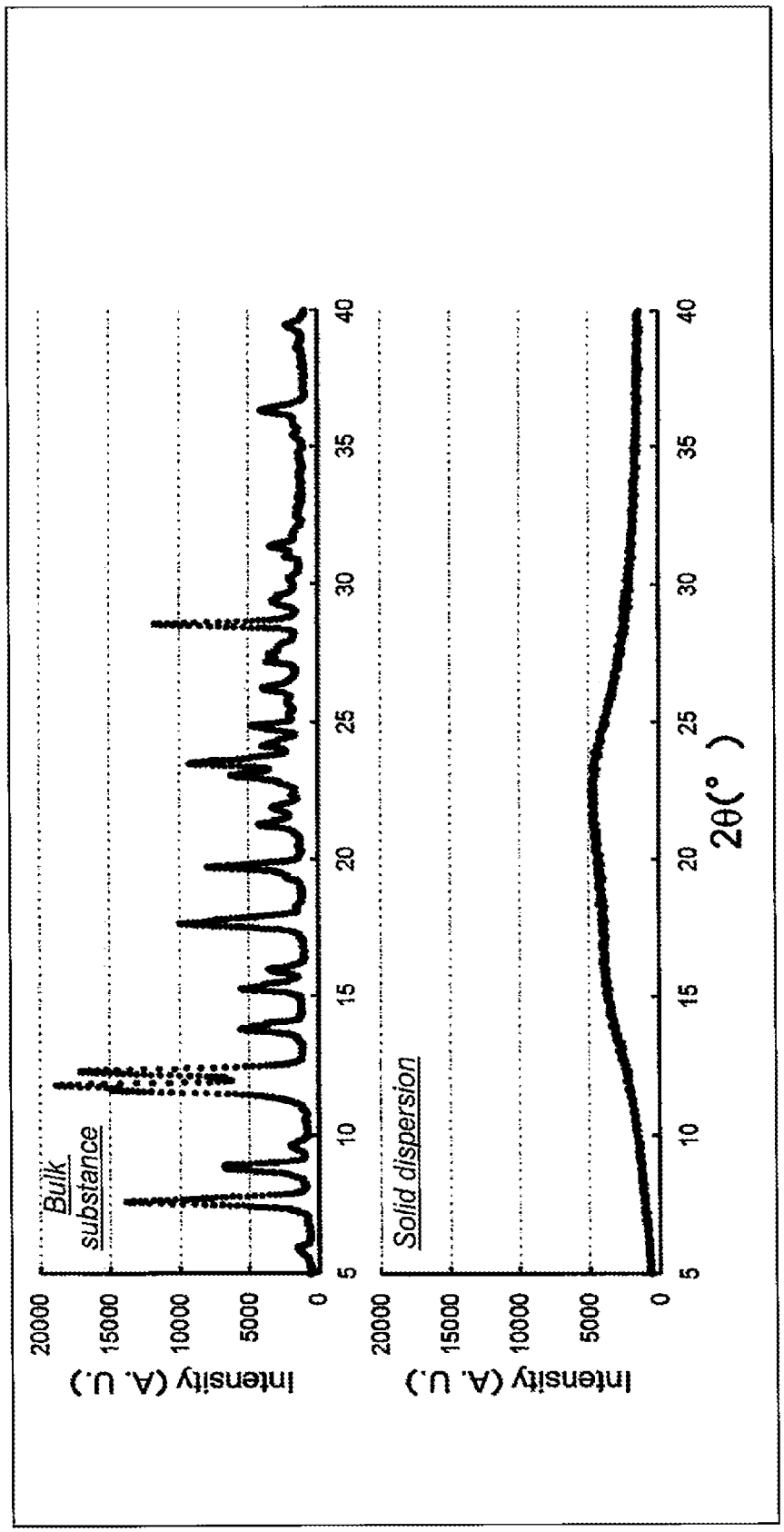
FIG. 2 is a diagram illustrating the results of nobiletin (upper graph) and nobiletin-methyl hesperidin solid dispersion (lower graph) according to Example 2 in powder X-ray diffraction.

Similarly to Example 1, from the result of the measurement by powder X-ray diffraction (FIG. 2), it was verified that nobiletin became amorphous in the solid dispersion. It is estimated that the solid dispersion has a degree of crystallization of 0%, and nobiletin has a degree of crystallization of 0%. The results of [Evaluation of solubility over time] and [Evaluation of Caco-2 cells membrane permeability] are shown in Table 1-1.

Example 3

Nobiletin (manufactured by Wako Pure Chemical Industries, Ltd.) as a poorly water-soluble substance and methyl hesperidin (manufactured by Tokyo Chemical Industry Co., Ltd.) were mixed in a proportion of 15% by mass and 85% by mass, respectively. Using this mixture, a solid dispersion was prepared in the same manner as in Example 1 (heating temperature: 160° C., heating time: 10 minutes, and the number of rotations of the screw: 80 r/min).

Figure 3:
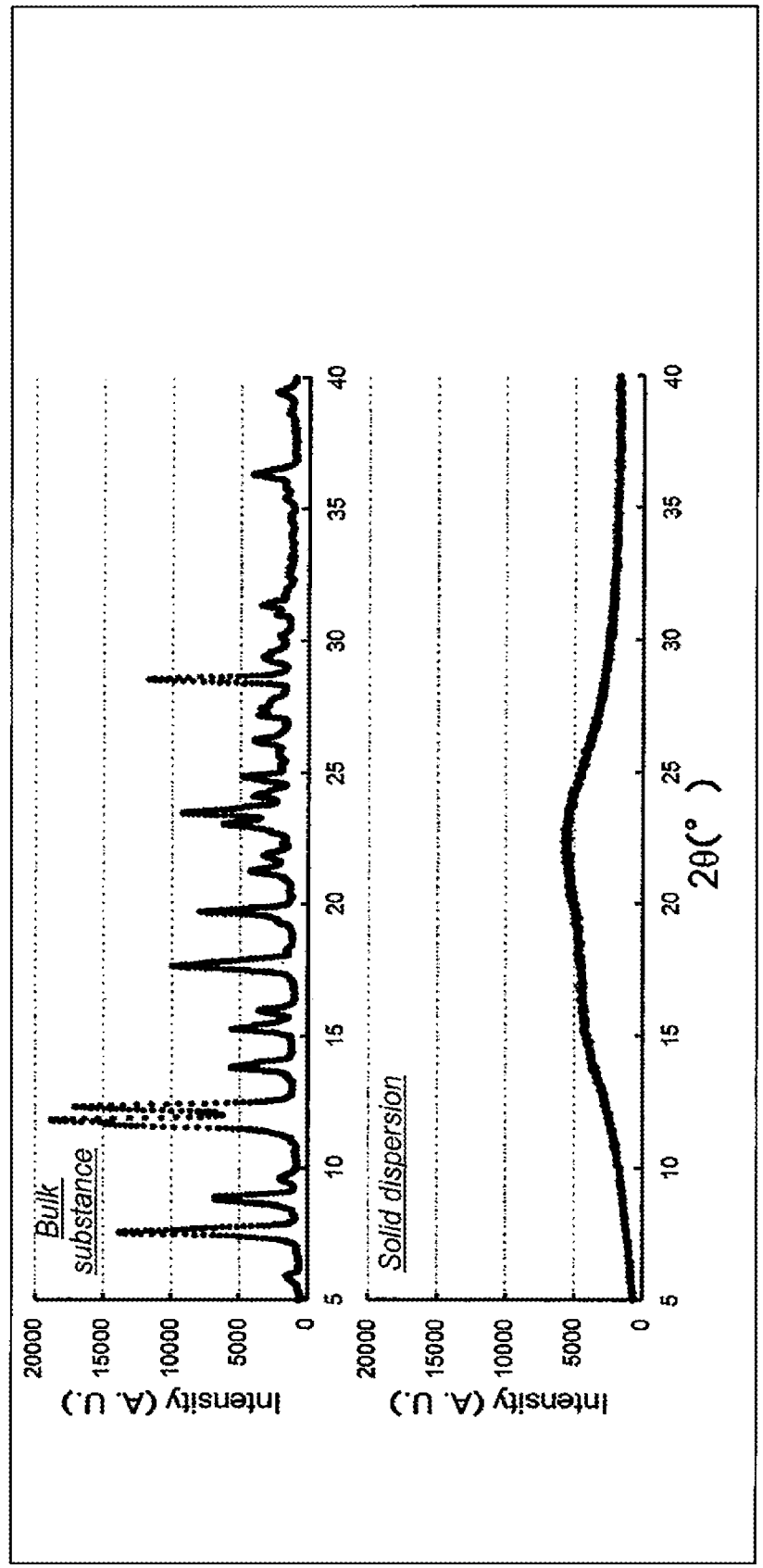
FIG. 3 is a diagram illustrating the results of nobiletin (upper graph) and nobiletin-methyl hesperidin solid dispersion (lower graph) according to Example 3 in powder X-ray diffraction.

Similarly to Example 1, from the result of the measurement by powder X-ray diffraction (FIG. 3), it was verified that nobiletin became amorphous in the solid dispersion. It is estimated that the solid dispersion has a degree of crystallization of 0%, and nobiletin has a degree of crystallization of 0%. The results of [Evaluation of solubility over time] and [Evaluation of Caco-2 cells membrane permeability] are shown in Table 1-1.

Example 4

Nobiletin (manufactured by Wako Pure Chemical Industries, Ltd.) as a poorly water-soluble substance and methyl hesperidin (manufactured by Tokyo Chemical Industry Co., Ltd.) were mixed in a proportion of 20% by mass and 80% by mass, respectively. Using this mixture, a solid dispersion was prepared in the same manner as in Example 1 (heating temperature: 160° C., heating time: 10 minutes, and the number of rotations of the screw: 80 r/min).

Figure 4:
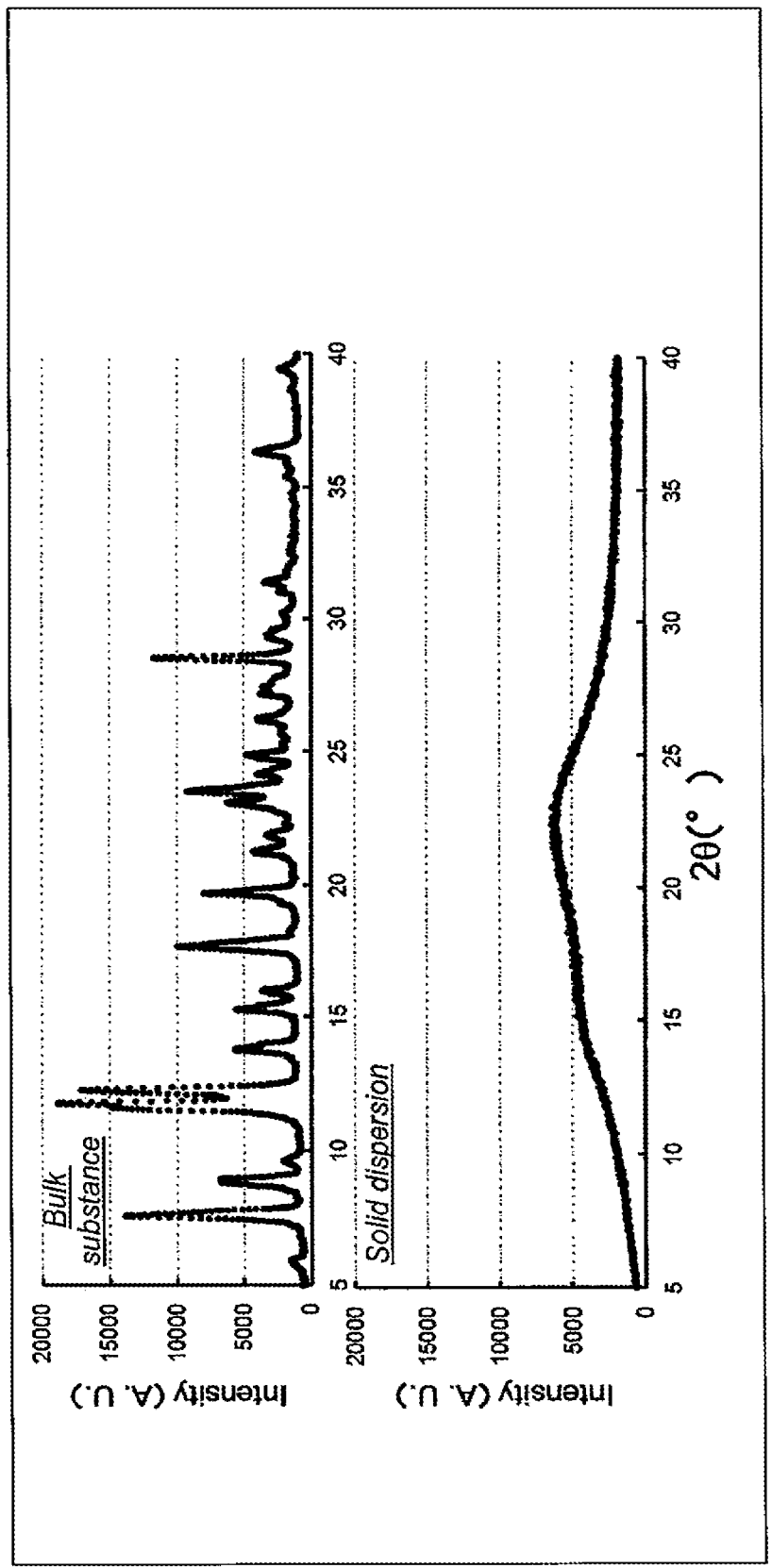
FIG. 4 is a diagram illustrating the results of nobiletin (upper graph) and nobiletin-methyl hesperidin solid dispersion (lower graph) according to Example 4 in powder X-ray diffraction.

Similarly to Example 1, from the result of the measurement by powder X-ray diffraction (FIG. 4), it was verified that nobiletin became amorphous in the solid dispersion. It is estimated that the solid dispersion has a degree of crystallization of 0%, and nobiletin has a degree of crystallization of 0%. The results of [Evaluation of solubility over time] and [Evaluation of Caco-2 cells membrane permeability] are shown in Table 1-1.

Example 5

Nobiletin (manufactured by Wako Pure Chemical Industries, Ltd.) as a poorly water-soluble substance and methyl hesperidin (manufactured by Tokyo Chemical Industry Co., Ltd.) were mixed in a proportion of 33% by mass and 67% by mass, respectively. Using this mixture, a solid dispersion was prepared in the same manner as in Example 1 (heating temperature: 160° C., heating time: 10 minutes, and the number of rotations of the screw: 80 r/min).

Figure 5:
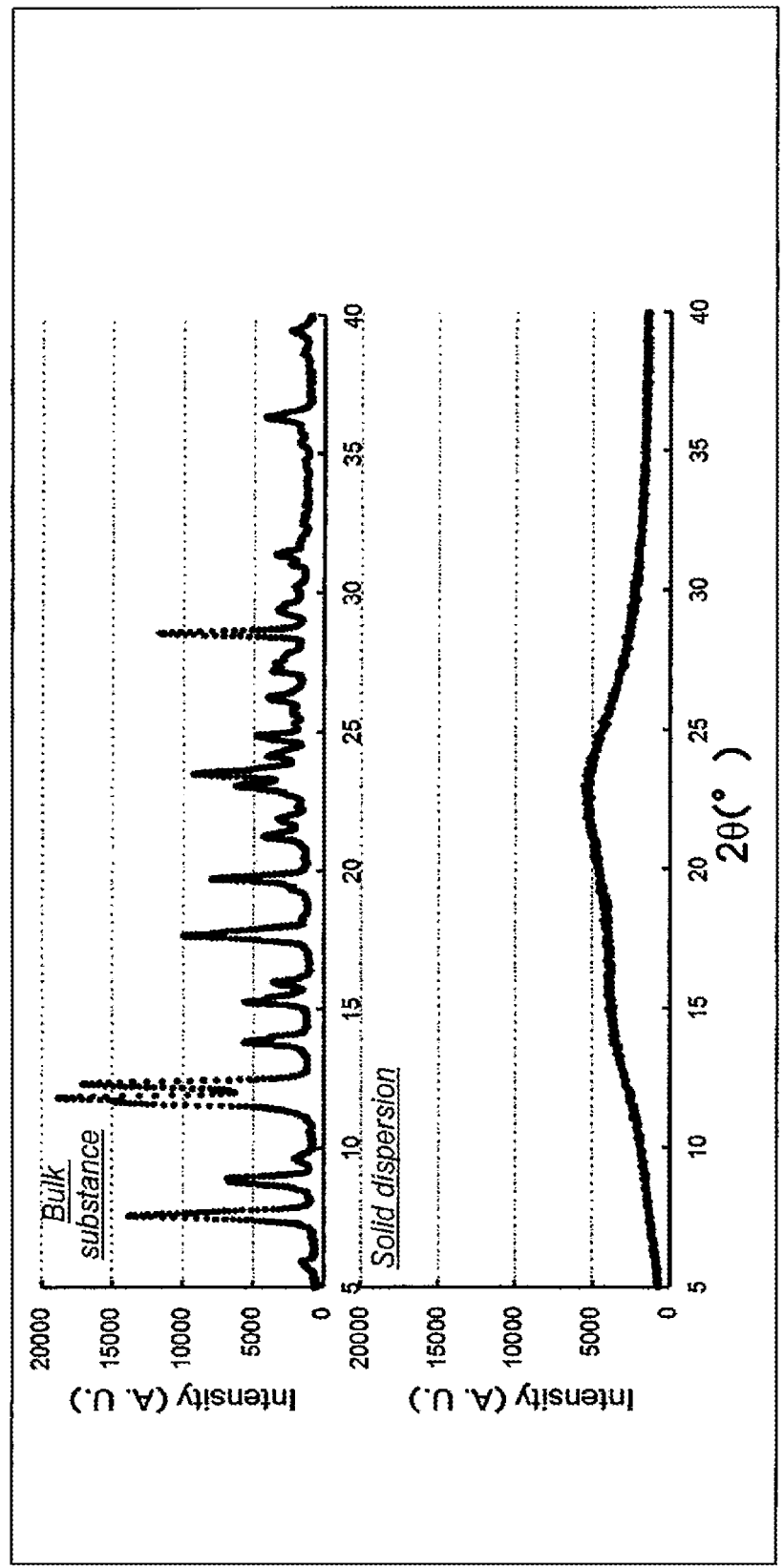
FIG. 5 is a diagram illustrating the results of nobiletin (upper graph) and nobiletin-methyl hesperidin solid dispersion (lower graph) according to Example 5 in powder X-ray diffraction.

Similarly to Example 1, from the result of the measurement by powder X-ray diffraction (FIG. 5), it was verified that nobiletin became amorphous in the solid dispersion. It is estimated that the solid dispersion has a degree of crystallization of 0%, and nobiletin has a degree of crystallization of 0%. The results of [Evaluation of solubility over time] and [Evaluation of Caco-2 cells membrane permeability] are shown in Table 1-1.

Example 6

Nobiletin (manufactured by Wako Pure Chemical Industries, Ltd.) as a poorly water-soluble substance and methyl hesperidin (manufactured by Tokyo Chemical Industry Co., Ltd.) were mixed in a proportion of 40% by mass and 60% by mass, respectively. Using this mixture, a solid dispersion was prepared in the same manner as in Example 1 (heating temperature: 160° C., heating time: 10 minutes, and the number of rotations of the screw: 80 r/min).

Similarly to Example 1, from the result of the measurement by powder X-ray diffraction (FIG. 6), it was verified that nobiletin became amorphous in the solid dispersion. It is estimated that the solid dispersion has a degree of crystallization of 0%, and nobiletin has a degree of crystallization of 0%. The results of [Evaluation of solubility over time] and [Evaluation of Caco-2 cells membrane permeability] are shown in Table 1-1.

Example 7

PMF90 (manufactured by Okinawa Research Center Co., Ltd., containing 60% nobiletin) as a poorly water-soluble substance and methyl hesperidin (manufactured by Tokyo Chemical Industry Co., Ltd.) were mixed in a proportion of 25% by mass and 75% by mass, respectively. Using this mixture, a solid dispersion was prepared in the same manner as in Example 1 (heating temperature: 160° C., heating time: 10 minutes, the number of rotations of the screw: 80 r/min).

Similarly to Example 1, from the result of the measurement by powder X-ray diffraction (FIG. 7), it was verified that the crystalline substance contained in PMF90 became amorphous in the solid dispersion. It is estimated that the solid dispersion has a degree of crystallization of 0%, and nobiletin has a degree of crystallization of 0%. The results of [Evaluation of solubility over time] and [Evaluation of Caco-2 cells membrane permeability] are shown in Table 1-1.

Example 8

PMF90 (manufactured by Okinawa Research Center Co., Ltd.) as a poorly water-soluble substance and methyl hesperidin (manufactured by Tokyo Chemical Industry Co., Ltd.) were mixed in a proportion of 10% by mass and 90% by mass, respectively. Using this mixture, a solid dispersion was prepared in the same manner as in Example 1 (heating temperature: 160° C., heating time: 10 minutes, the number of rotations of the screw: 80 r/min).

Figure 8:
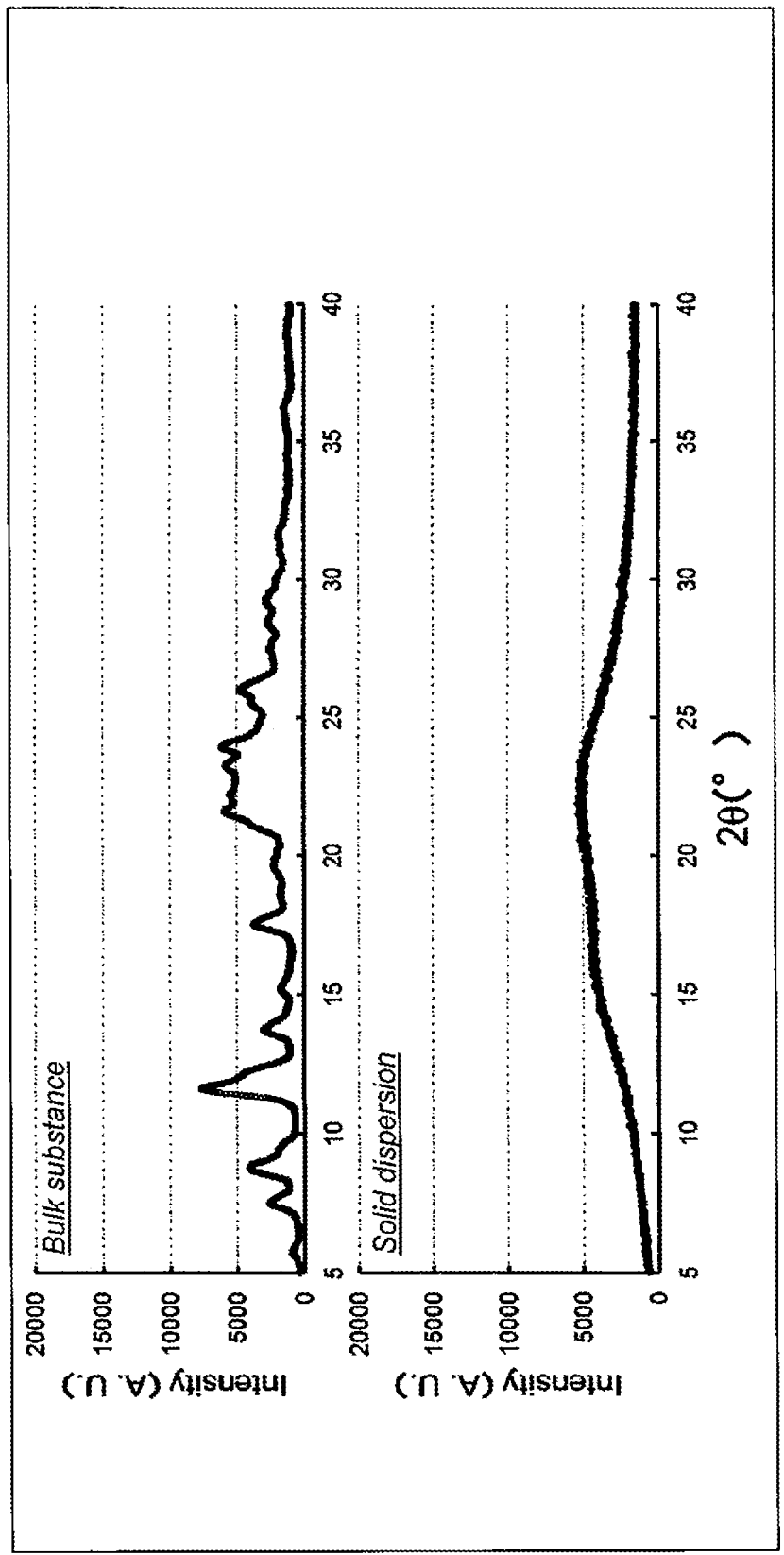
FIG. 8 is a diagram illustrating the results of PMF90 (upper graph) and PMF90-methyl hesperidin solid dispersion (lower graph) according to Example 8 in powder X-ray diffraction.

Similarly to Example 1, from the result of the measurement by powder X-ray diffraction (FIG. 8), it was verified that the crystalline substance contained in PMF90 became amorphous in the solid dispersion. It is estimated that the solid dispersion has a degree of crystallization of 0%, and nobiletin has a degree of crystallization of 0%. The results of [Evaluation of solubility over time] and [Evaluation of Caco-2 cells membrane permeability] are shown in Table 1-1.

Example 9

PMF90 (manufactured by Okinawa Research Center Co., Ltd.) as a poorly water-soluble substance and methyl hesperidin (manufactured by Tokyo Chemical Industry Co., Ltd.) were mixed in a proportion of 33% by mass and 67% by mass, respectively. Using this mixture, a solid dispersion was prepared in the same manner as in Example 1 (heating temperature: 160° C., heating time: 10 minutes, the number of rotations of the screw: 80 r/min).

Figure 9:
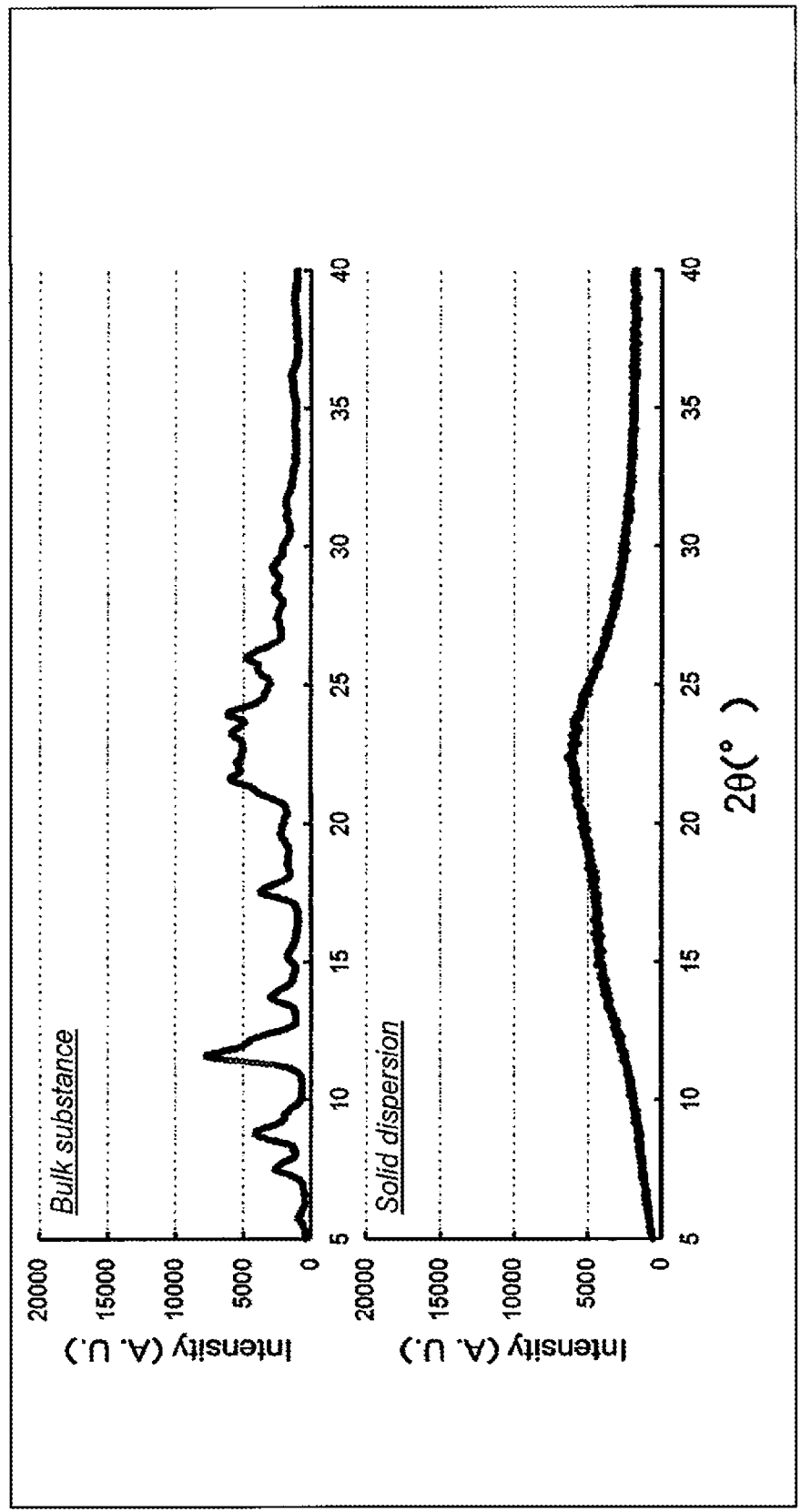
FIG. 9 is a diagram illustrating the results of PMF90 (upper graph) and PMF90-methyl hesperidin solid dispersion (lower graph) according to Example 9 in powder X-ray diffraction.

Similarly to Example 1, from the result of the measurement by powder X-ray diffraction (FIG. 9), it was verified that the crystalline substance contained in PMF90 became amorphous in the solid dispersion. It is estimated that the solid dispersion has a degree of crystallization of 0%, and nobiletin has a degree of crystallization of 0%. The results of [Evaluation of solubility over time] and [Evaluation of Caco-2 cells membrane permeability] are shown in Table 1-1.

Example 10

PMF90 (manufactured by Okinawa Research Center Co., Ltd.) as a poorly water-soluble substance and methyl hesperidin (manufactured by Tokyo Chemical Industry Co., Ltd.) were mixed in a proportion of 40% by mass and 60% by mass, respectively. Using this mixture, a solid dispersion was prepared in the same manner as in Example 1 (heating temperature: 160° C., heating time: 10 minutes, the number of rotations of the screw: 80 r/min).

Figure 10:
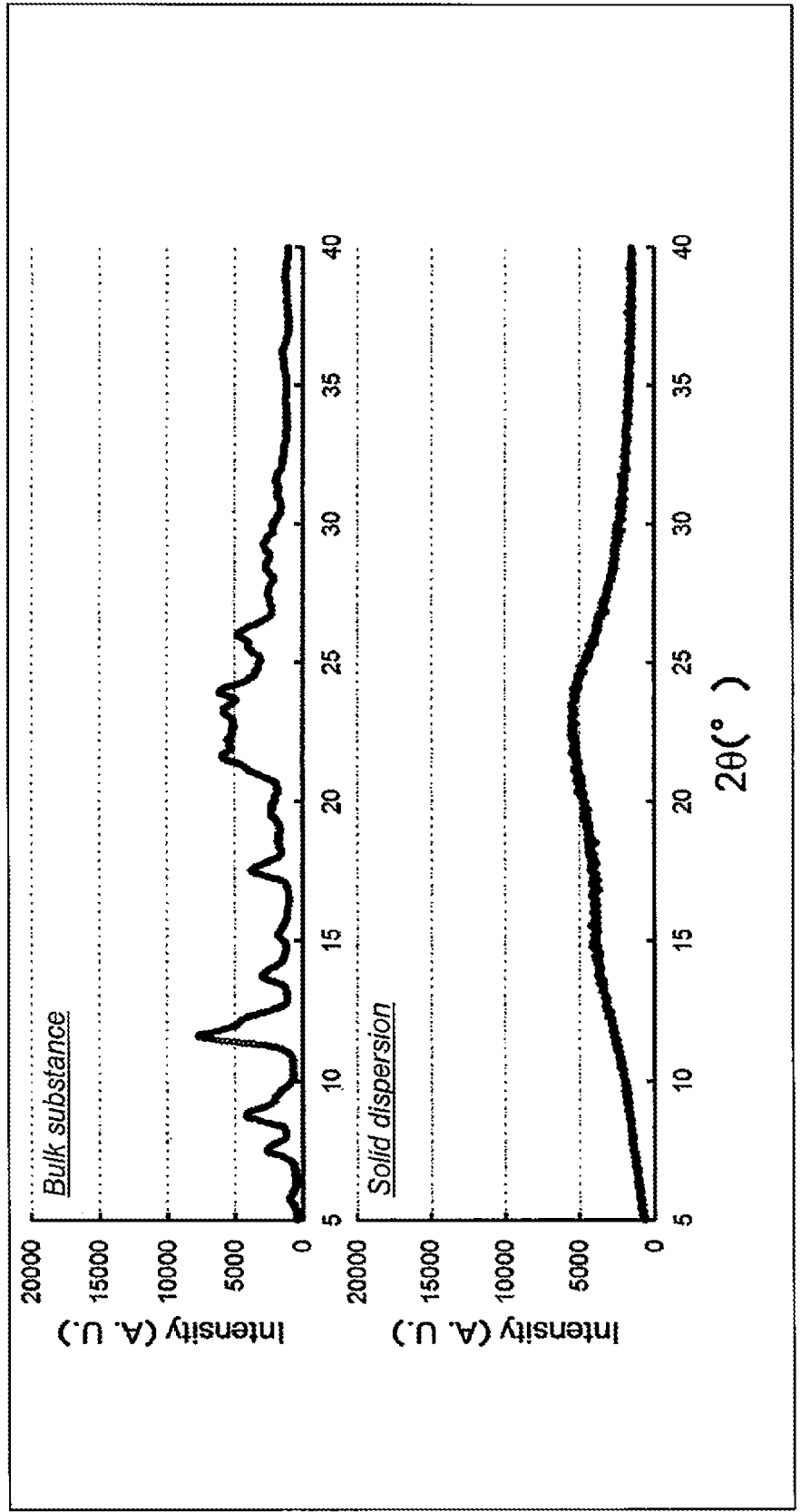
FIG. 10 is a diagram illustrating the results of PMF90 (upper graph) and PMF90-methyl hesperidin solid dispersion (lower graph) according to Example 10 in powder X-ray diffraction.

Similarly to Example 1, from the result of the measurement by powder X-ray diffraction (FIG. 10), it was verified that the crystalline substance contained in PMF90 became amorphous in the solid dispersion. It is estimated that the solid dispersion has a degree of crystallization of 0%, and nobiletin has a degree of crystallization of 0%. The results of [Evaluation of solubility over time] and [Evaluation of Caco-2 cells membrane permeability] are shown in Table 1-1.

Example 11

PMF90 (manufactured by Okinawa Research Center Co., Ltd.) as a poorly water-soluble substance and methyl hesperidin (manufactured by Tokyo Chemical Industry Co., Ltd.) were mixed in a proportion of 60% by mass and 40% by mass, respectively. Using this mixture, a solid dispersion was prepared in the same manner as in Example 1 (heating temperature: 160° C., heating time: 10 minutes, the number of rotations of the screw; 80 r/min).

Figure 11:
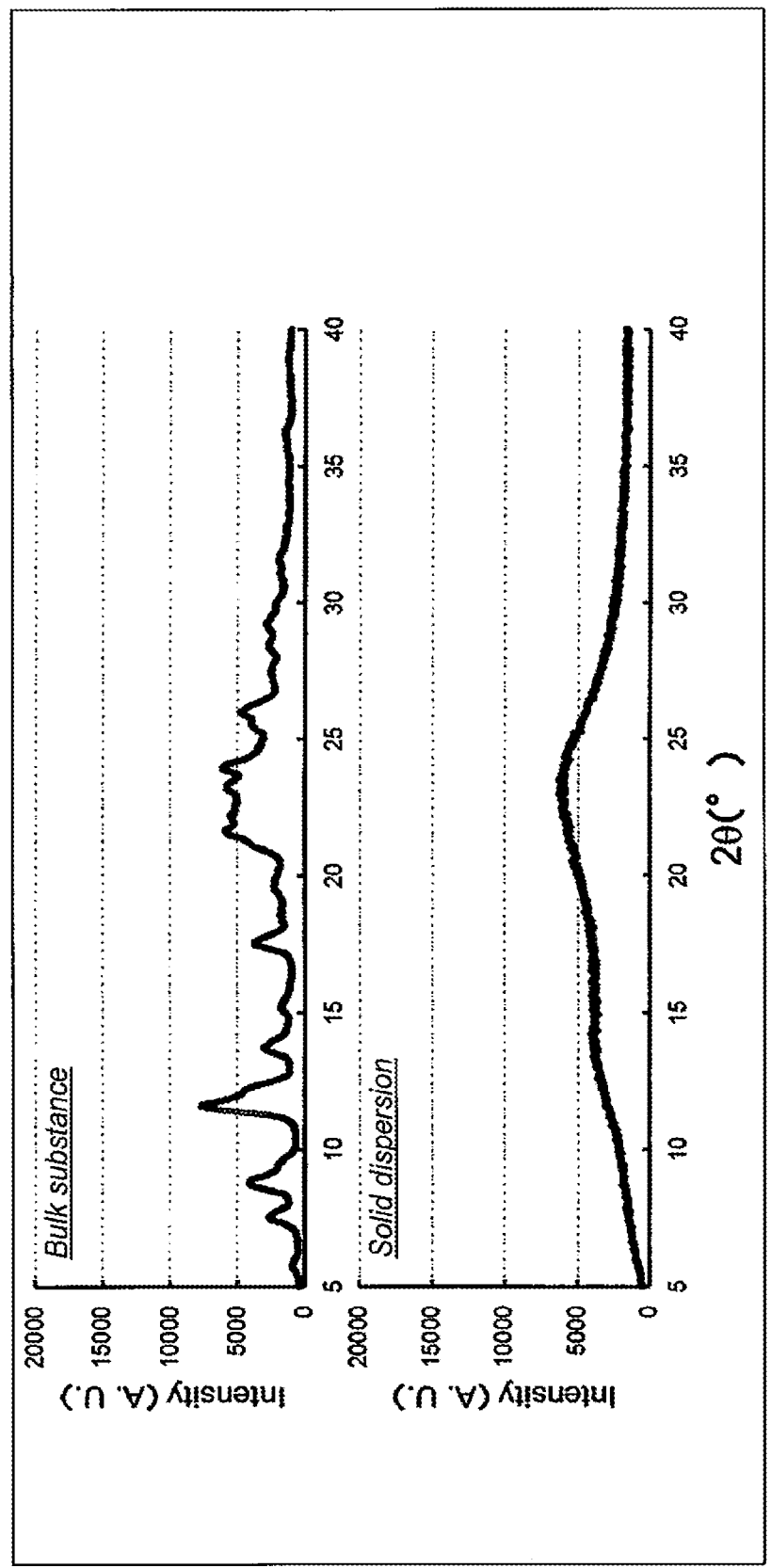
FIG. 11 is a diagram illustrating the results of PMF90 (upper graph) and PMF90-methyl hesperidin solid dispersion (lower graph) according to Example 11 in powder X-ray diffraction.

Similarly to Example 1, from the result of the measurement by powder X-ray diffraction (FIG. 11), it was verified that the crystalline substance contained in PMF90 became amorphous in the solid dispersion. It is estimated that the solid dispersion has a degree of crystallization of 0%, and nobiletin has a degree of crystallization of 0%. The results of [Evaluation of solubility over time] and [Evaluation of Caco-2 cells membrane permeability] are shown in Table 1-1.

Example 12

PMF90 (manufactured by Okinawa Research Center Co., Ltd.) as a poorly water-soluble substance and methyl hesperidin (manufactured by Tokyo Chemical Industry Co., Ltd.) were mixed in a proportion of 67% by mass and 33% by mass, respectively. Using this mixture, a solid dispersion was prepared in the same manner as in Example 1 (heating temperature: 160° C., heating time: 10 minutes, the number of rotations of the screw: 80 r/min).

Figure 12:
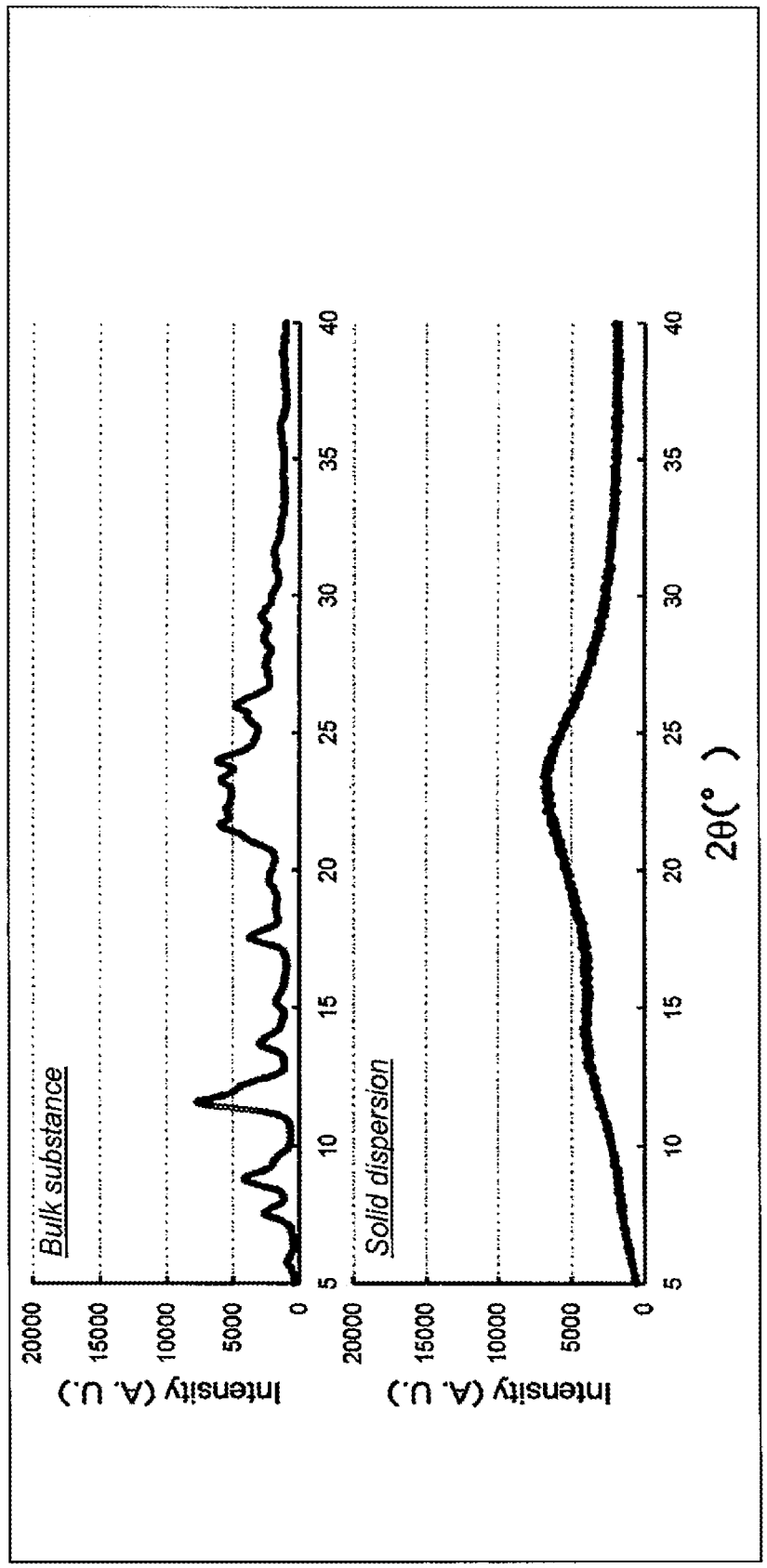
FIG. 12 is a diagram illustrating the results of PMF90 (upper graph) and PMF90-methyl hesperidin solid dispersion (lower graph) according to Example 12 in powder X-ray diffraction.

Similarly to Example 1, from the result of the measurement by powder X-ray diffraction (FIG. 12), it was verified that the crystalline substance contained in PMF90 became amorphous in the solid dispersion. It is estimated that the solid dispersion has a degree of crystallization of 0%, and nobiletin has a degree of crystallization of 0%. The results of [Evaluation of solubility over time] and [Evaluation of Caco-2 cells membrane permeability] are shown in Table 1-1.

Example 13

PMF90 (manufactured by Okinawa Research Center Co., Ltd.) as a poorly water-soluble substance and monoglucosyl hesperidin (hereinafter, referred to as mGHes, refined product prepared by refining the product of Toyo Sugar Refining Co., Ltd., αG hesperidin PA-T by the method above using HPLC) were mixed in a proportion of 25% by mass and 75% by mass, respectively. Using this mixture, a solid dispersion was prepared in the same manner as in Example 1 (heating temperature: 160° C., heating time: 10 minutes, the number of rotations of the screw: 80 r/min).

Figure 13:
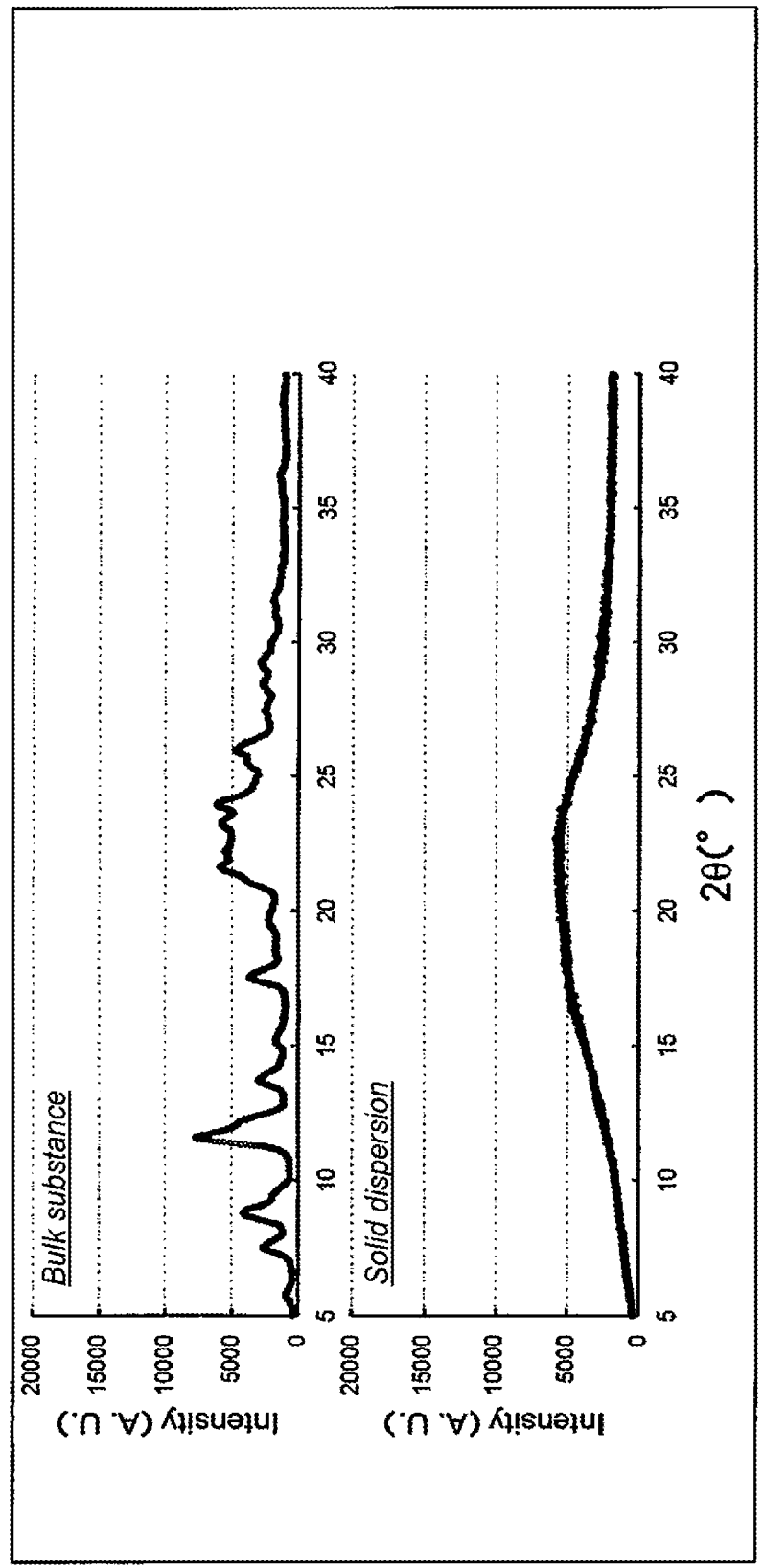
FIG. 13 is a diagram illustrating the results of PMF90 (upper graph) and PMF90-mGHes solid dispersion (lower graph) according to Example 13 in powder X-ray diffraction.

Similarly to Example 1, from the result of the measurement by powder X-ray diffraction (FIG. 13), it was verified

23 that the crystalline substance contained in PMF90 became amorphous in the solid dispersion. It is estimated that the solid dispersion has a degree of crystallization of 0%, and nobiletin has a degree of crystallization of 0%. The results of [Evaluation of solubility over time] and [Evaluation of Caco-2 cells membrane permeability] are shown in Table 1-1.

Example 14

PMF90 (manufactured by Okinawa Research Center Co., Ltd.) as a poorly water-soluble substance and mGHes were mixed in a proportion of 33% by mass and 67% by mass, respectively. Using this mixture, a solid dispersion was prepared in the same manner as in Example 1 (heating temperature: 160° C., heating time: 10 minutes, the number of rotations of the screw: 80 r/min).

Figure 14:
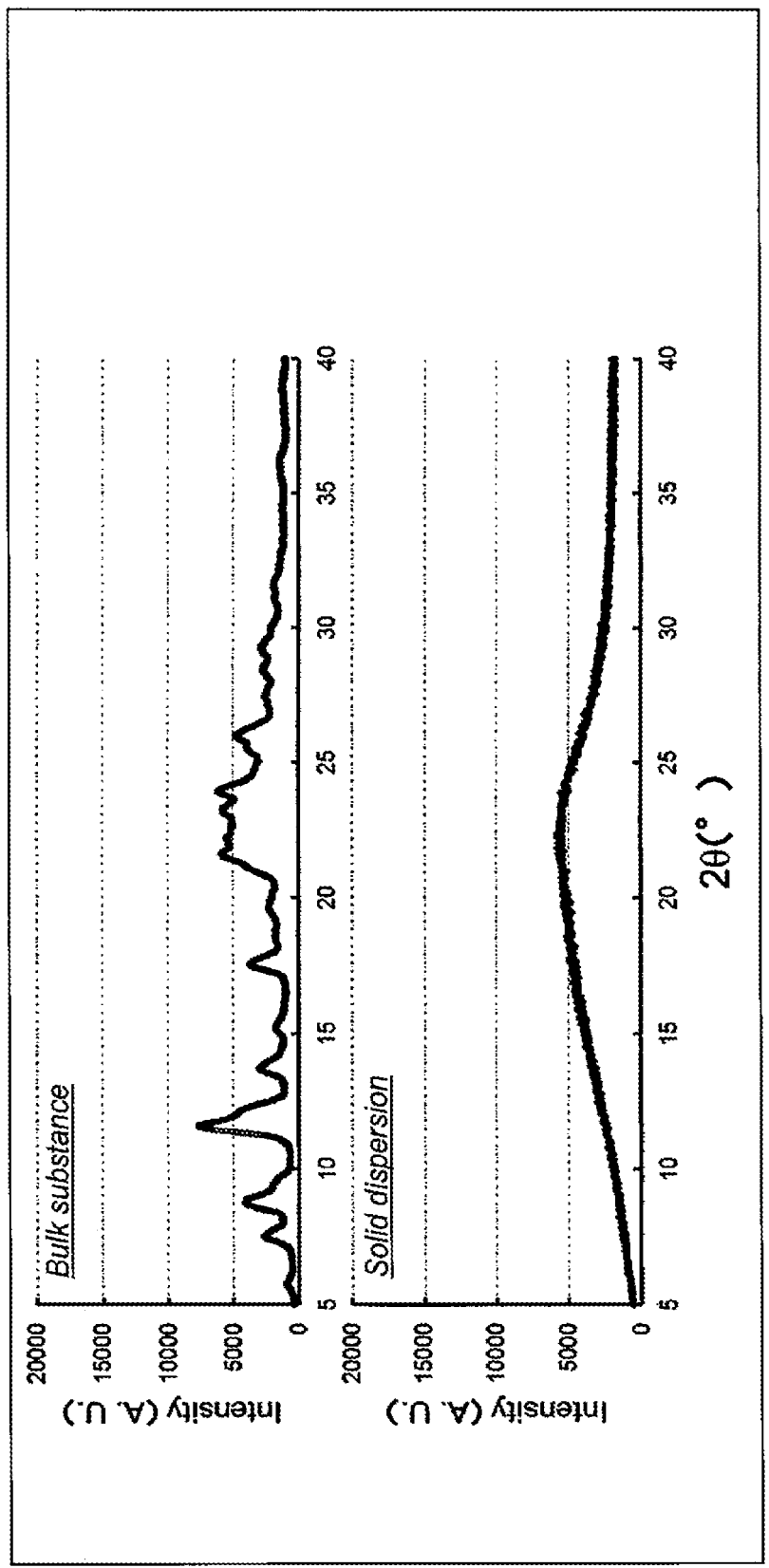
FIG. 14 is a diagram illustrating the results of PMF90 (upper graph) and PMF90-mGHes solid dispersion (lower graph) according to Example 14 in powder X-ray diffraction.

Similarly to Example 1, from the result of the measurement by powder X-ray diffraction (FIG. 14), it was verified that the crystalline substance contained in PMF90 became amorphous in the solid dispersion. It is estimated that the solid dispersion has a degree of crystallization of 0%, and nobiletin has a degree of crystallization of 0%. The results of [Evaluation of solubility over time] and [Evaluation of Caco-2 cells membrane permeability] are shown in Table 1-1.

Example 15

PMF90 (manufactured by Okinawa Research Center Co., Ltd.) as a poorly water-soluble substance and αG hesperidin PA-T (manufactured by Toyo Sugar Refining Co., Ltd.) were mixed in a proportion of 25% by mass and 75% by mass, respectively. Using this mixture, a solid dispersion was prepared in the same manner as in Example 1 (heating temperature: 160° C., heating time: 10 minutes, the number of rotations of the screw: 80 r/min).

Figure 15:
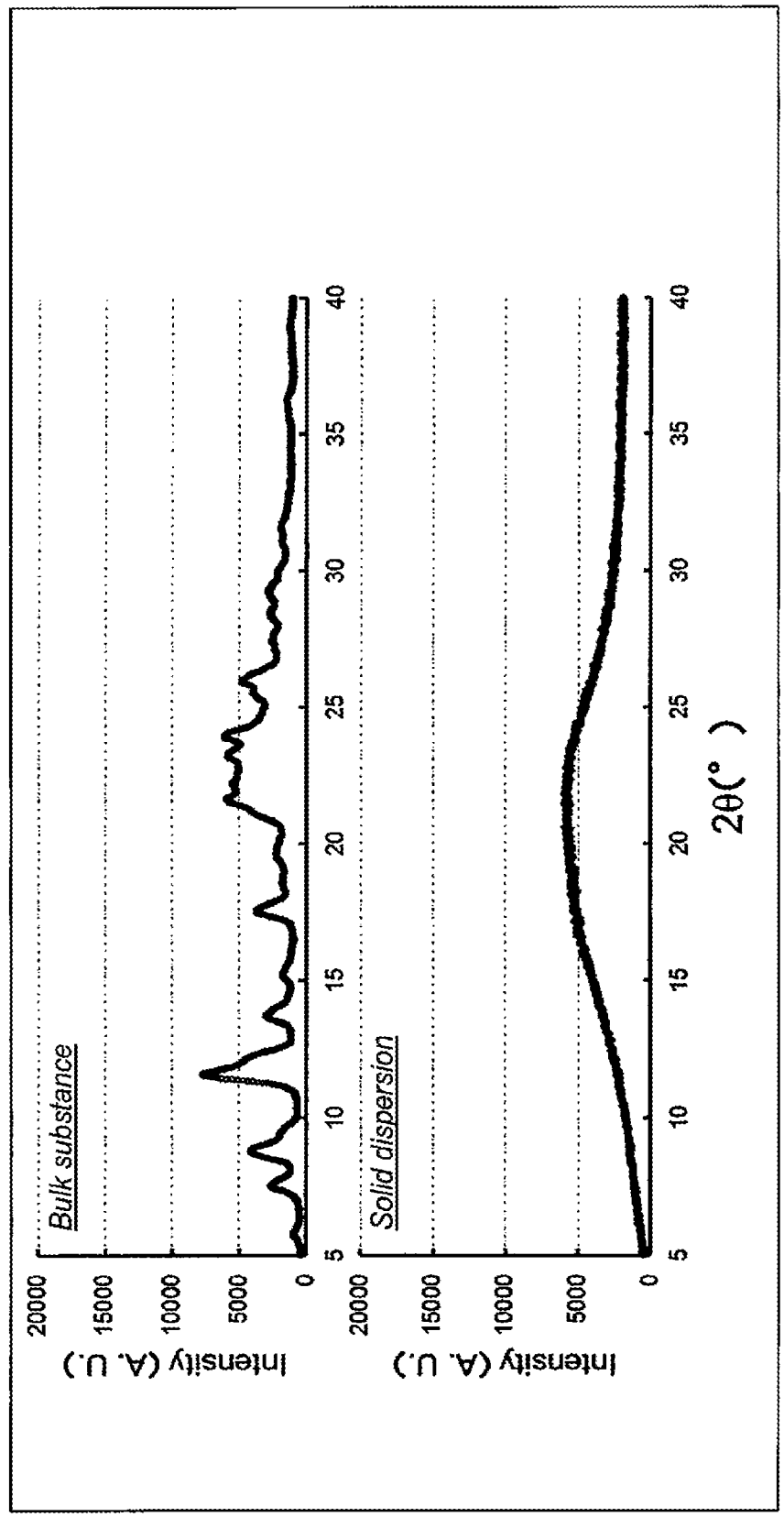
FIG. 15 is a diagram illustrating the results of PMF90 (upper graph) and PMF90-aG hesperidin PA-T solid dispersion (lower graph) according to Example 15 in powder X-ray diffraction.

Similarly to Example 1, from the result of the measurement by powder X-ray diffraction (FIG. 15), it was verified that the crystalline substance contained in PMF90 became amorphous in the solid dispersion. It is estimated that the solid dispersion has a degree of crystallization of 0%, and nobiletin has a degree of crystallization of 0%. The results of [Evaluation of solubility over time] and [Evaluation of Caco-2 cells membrane permeability] are shown in Table 1-1.

Example 16

PMF90 (manufactured by Okinawa Research Center Co., Ltd.) as a poorly water-soluble substance and αG hesperidin PA-T (manufactured by Toyo Sugar Refining Co., Ltd.) were mixed in a proportion of 33% by mass and 67% by mass, respectively. Using this mixture, a solid dispersion was prepared in the same manner as in Example 1 (heating temperature: 160° C., heating time: 10 minutes, the number of rotations of the screw: 80 r/min).

Figure 16:
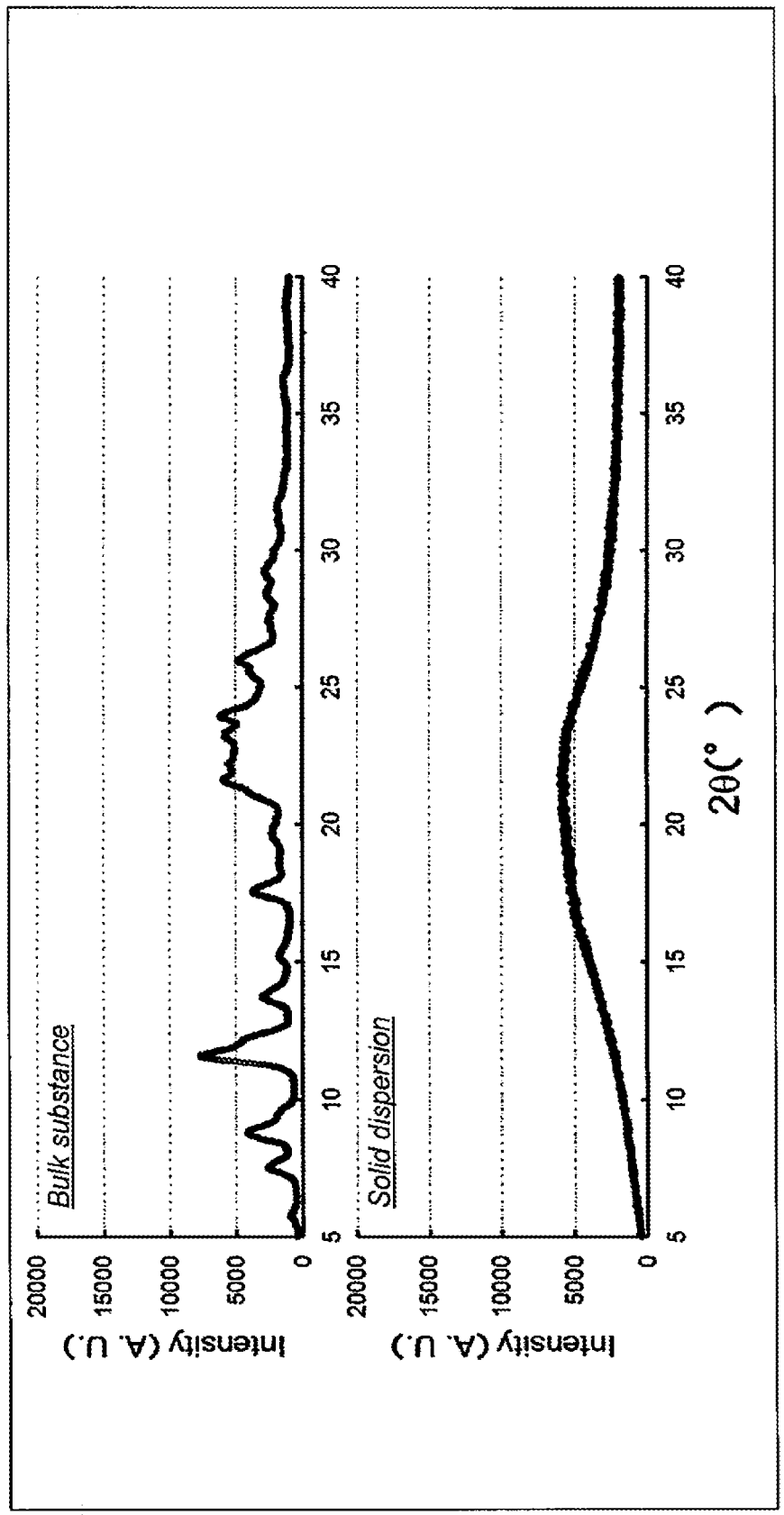
FIG. 16 is a diagram illustrating the results of PMF90 (upper graph) and PMF90-αG hesperidin PA-T solid dispersion (lower graph) according to Example 16 in powder X-ray diffraction.

Similarly to Example 1, from the result of the measurement by powder X-ray diffraction (FIG. 16), it was verified that the crystalline substance contained in PMF90 became amorphous in the solid dispersion. It is estimated that the solid dispersion has a degree of crystallization of 0%, and nobiletin has a degree of crystallization of 0%. The results of [Evaluation of solubility over time] and [Evaluation of Caco-2 cells membrane permeability] are shown in Table 1-1.

24

Comparative Example 1

Ellagic acid dihydrate (Tokyo Chemical Industry Co., Ltd.) as a poorly water-soluble substance and methyl hesperidin (manufactured by Tokyo Chemical Industry Co., Ltd.) were mixed in a proportion of 25% by mass and 75% by mass, respectively. Using this mixture, a solid dispersion was prepared in the same manner as in Example 1 (heating temperature: 160° C., heating time: 10 minutes, the number of rotations of the screw: 80 r/min).

Figure 17:
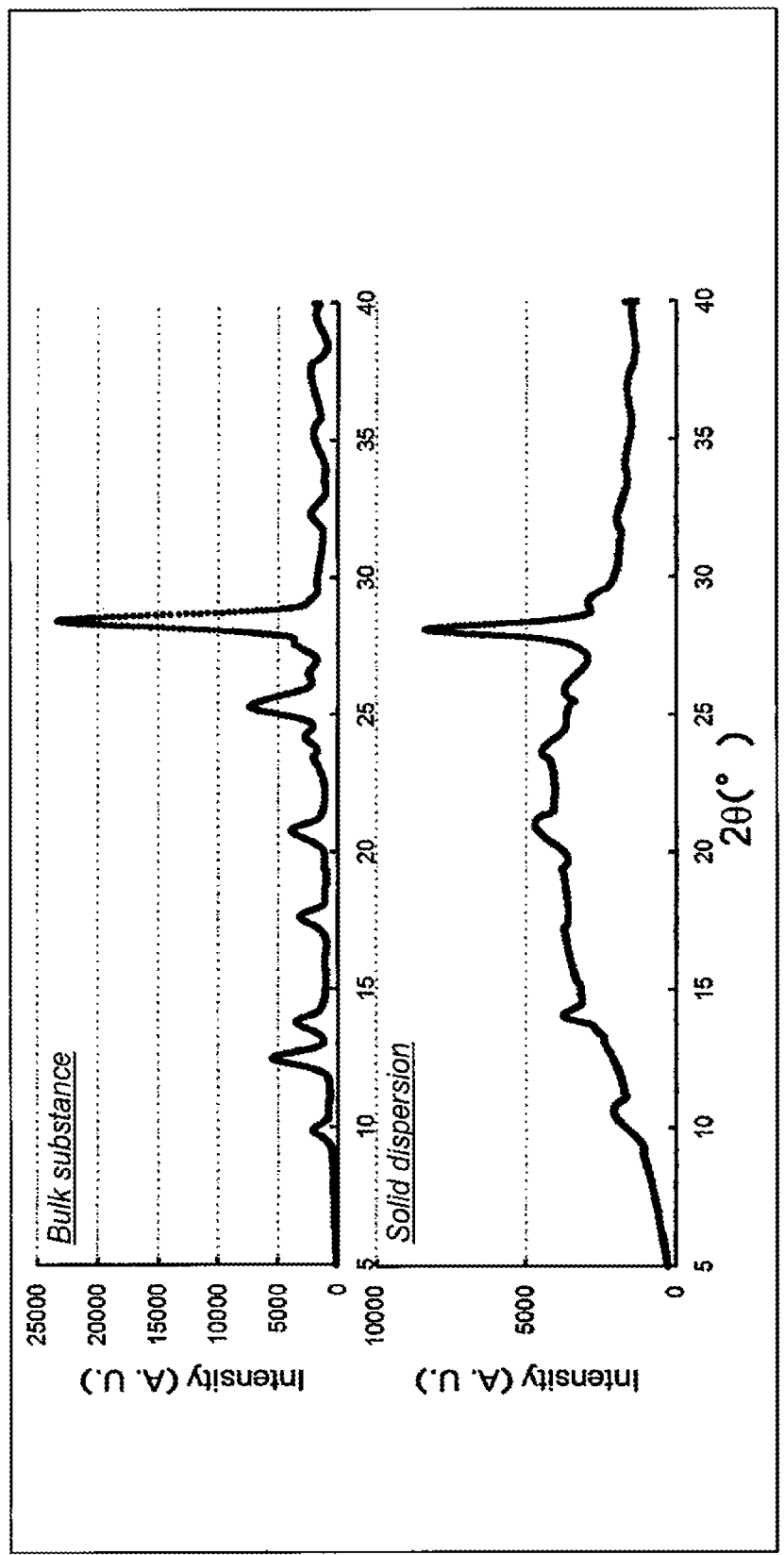
FIG. 17 is a diagram illustrating the results of ellagic acid (upper graph) and ellagic acid-methyl hesperidin solid dispersion (prepared at 160° C., lower graph) according to Comparative Example 1 in powder X-ray diffraction.

Similarly to Example 1, from the result of the measurement by powder X-ray diffraction (FIG. 17), it was verified that ellagic acid became amorphous in the solid dispersion. The results of [Evaluation of solubility over time] and [Evaluation of Caco-2 cells membrane permeability] are shown in FIG. 6 and Table 1-2.

Comparative Example 2

Figure 18:
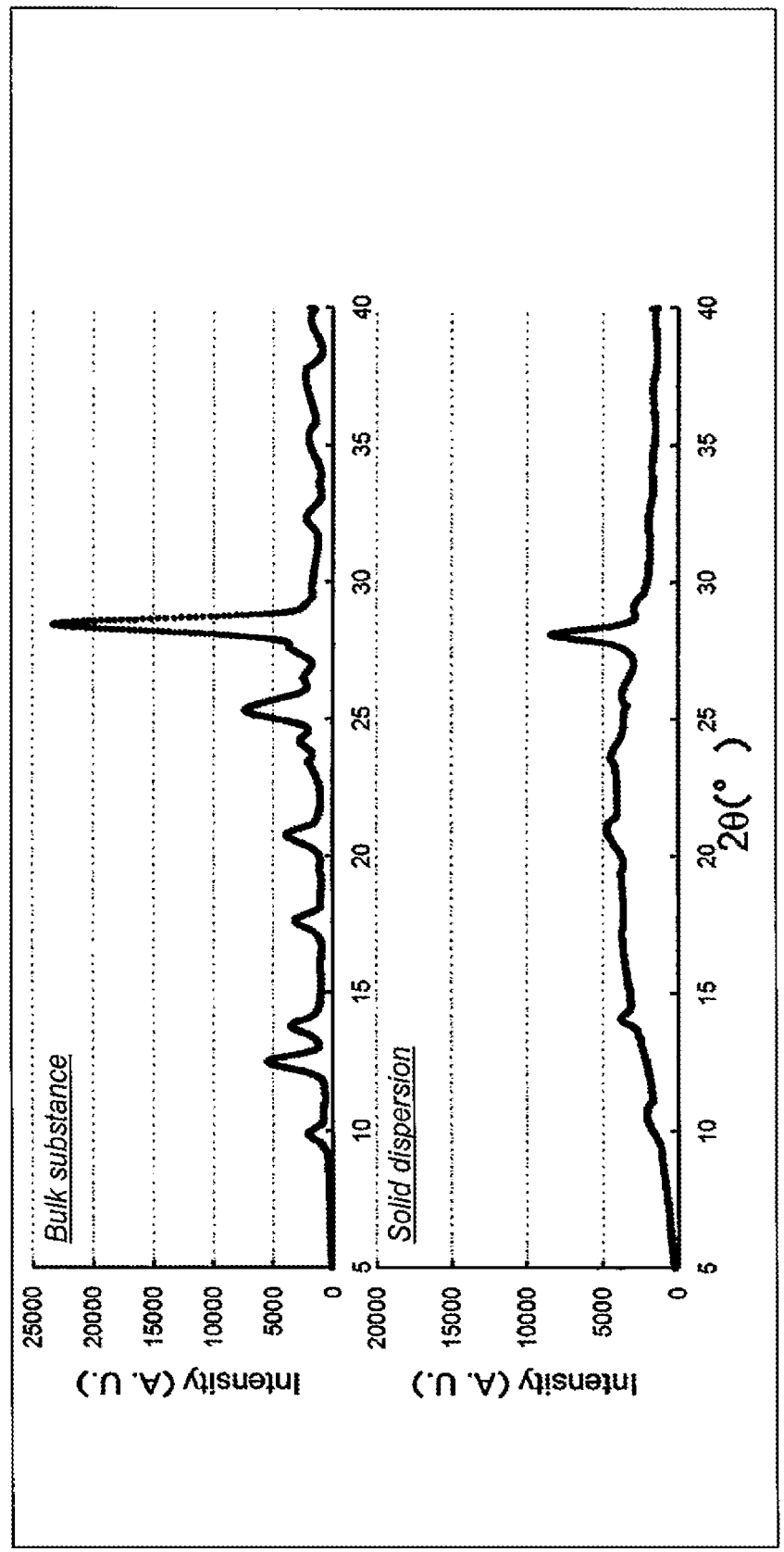
FIG. 18 is a diagram illustrating the results of ellagic acid (upper graph) and ellagic acid-methyl hesperidin solid dispersion (prepared at 180° C., lower graph) according to Comparative Example 2 in powder X-ray diffraction.

Ellagic acid dihydrate (manufactured by Tokyo Chemical Industry Co., Ltd.) as a poorly water-soluble substance and methyl hesperidin (manufactured by Tokyo Chemical Industry Co., Ltd.) were mixed in a proportion of 25% by mass and 75% by mass, respectively. Using this mixture, a solid dispersion was prepared in the same manner as in Example 1 (heating temperature: 180° C., heating time: 10 minutes, the number of rotations of the screw: 80 r/min). Similarly to Example 1, from the result of the measurement by powder X-ray diffraction (FIG. 18), it was verified that ellagic acid became amorphous in the solid dispersion. The results of [Evaluation of solubility over time] and [Evaluation of Caco-2 cells membrane permeability] are shown in FIG. 6 and Table 1-2.

Comparative Example 3

Figure 19:
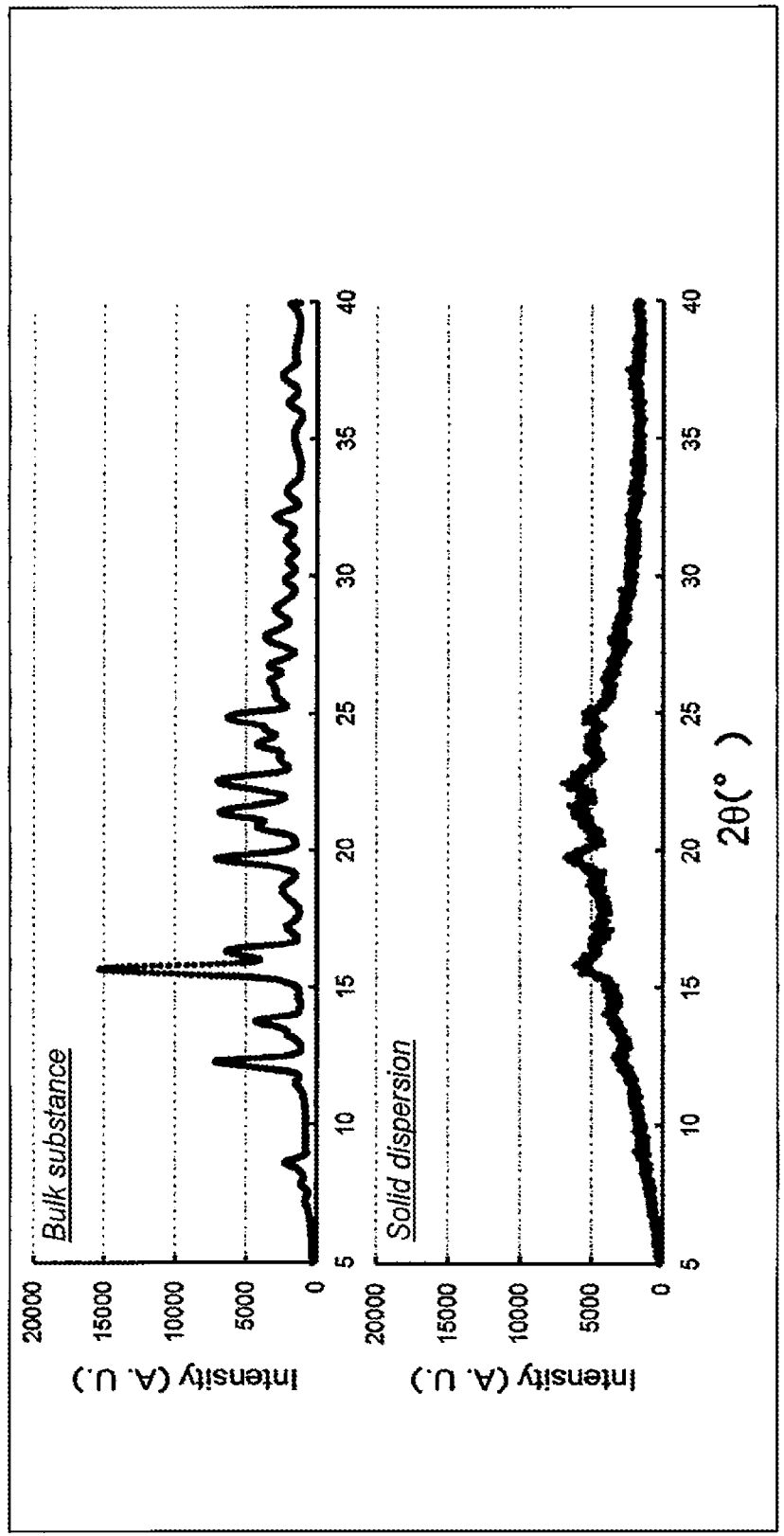
FIG. 19 is a diagram illustrating the results of sesamin (upper graph) and sesamin-methyl hesperidin solid dispersion (lower graph) according to Comparative Example 3 in powder X-ray diffraction.

Sesamin (manufactured by CHROMADEX INC.) as a poorly water-soluble substance and methyl hesperidin (manufactured by Tokyo Chemical Industry Co., Ltd.) were mixed in a proportion of 25% by mass and 75% by mass, respectively. Using this mixture, a solid dispersion was prepared in the same manner as in Example 1 (heating temperature: 160° C., heating time: 10 minutes, the number of rotations of the screw: 80 r/min). Similarly to Example 1, from the result of the measurement by powder X-ray diffraction (FIG. 19), it was verified that sesamin became amorphous in the solid dispersion. The results of [Evaluation of solubility over time] and [Evaluation of Caco-2 cells membrane permeability] are shown in FIG. 6 and Table 1-2.

Comparative Example 4

Figure 20:
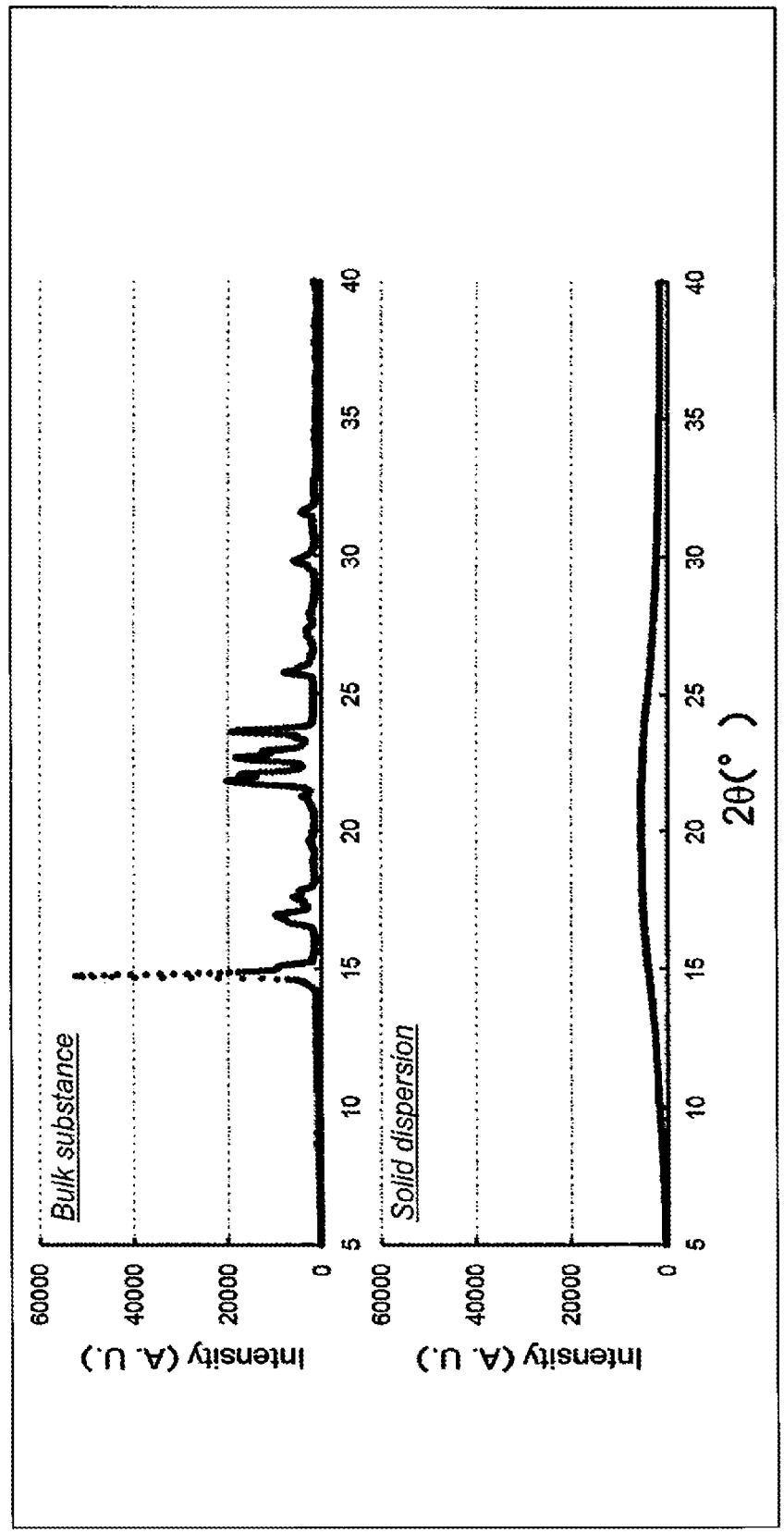
FIG. 20 is a diagram illustrating the results of hesperidin (upper graph) and hesperidin-methyl hesperidin solid dispersion (lower graph) according to Comparative Example 4 in powder X-ray diffraction.

Hesperidin (manufactured by Tokyo Chemical Industry Co., Ltd.) as a poorly water-soluble substance and methyl hesperidin (manufactured by Tokyo Chemical Industry Co., Ltd.) were mixed in a proportion of 25% by mass and 75% by mass, respectively. Using this mixture, a solid dispersion was prepared in the same manner as in Example 1 (heating temperature: 160° C., heating time: 10 minutes, the number of rotations of the screw: 80 r/min). Similarly to Example 1, from the result of the measurement by powder X-ray diffraction (FIG. 20), it was verified that hesperidin became amorphous in the solid dispersion. The results of [Evaluation of solubility over time] and [Evaluation of Caco-2 cells membrane permeability] are shown in FIG. 6 and Table 1-2.

Comparative Example 5

Figure 21:
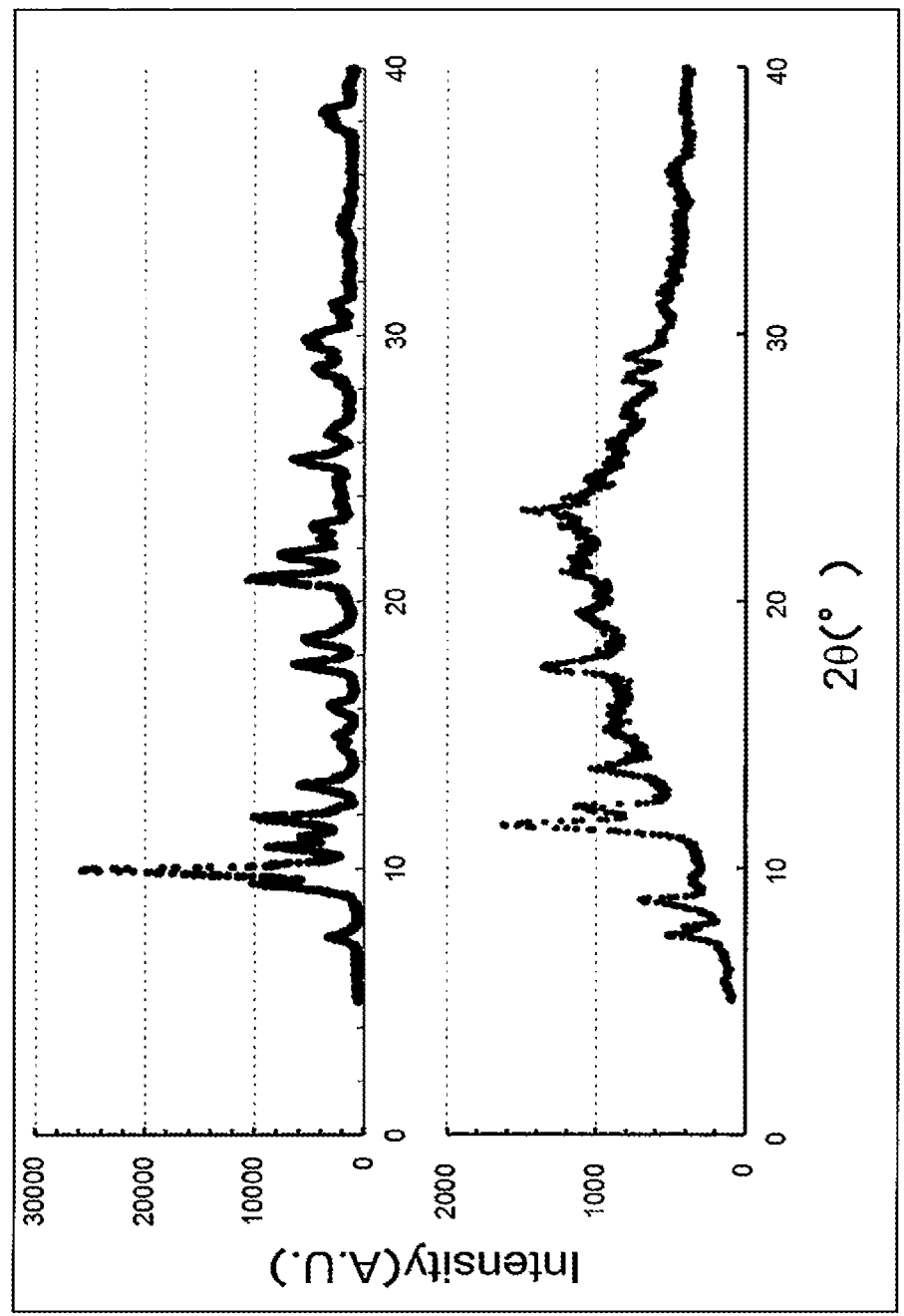
FIG. 21 is a diagram illustrating the results of nobiletin (upper graph) and nobiletin-methyl hesperidin mixture (lower graph) according to Comparative Example 4 in powder X-ray diffraction.

A mixture of nobiletin (manufactured by Wako Pure Chemical Industries, Ltd.) as a poorly water-soluble substance and methyl hesperidin (manufactured by Tokyo Chemical Industry Co., Ltd.) in a proportion of 25% by mass and 75% by mass, respectively, was evaluated. Form the results in the measurement by powder X-ray diffraction (FIG. 21), it was verified that nobiletin was present in the form of crystal in the mixture. The results of [Evaluation of solubility over time] and [Evaluation of Caco-2 cells membrane permeability] are shown in Table 1-2.

Comparative Example 6

A mixture of PMF90 (manufactured by Okinawa Research Center Co., Ltd.) as a poorly water-soluble substance and methyl hesperidin (manufactured by Tokyo Chemical Industry Co., Ltd.) in a proportion of 25% by mass and 75% by mass, respectively, was evaluated. The results of [Evaluation of solubility over time] and [Evaluation of Caco-2 cells membrane permeability] are shown in Table 1-2.

Comparative Example 7

A mixture of PMF90 (manufactured by Okinawa Research Center Co., Ltd.) as a poorly water-soluble substance and methyl hesperidin (manufactured by Tokyo Chemical Industry Co., Ltd.) in a proportion of 40% by mass and 60% by mass, respectively, was evaluated. The results of [Evaluation of solubility over time] and [Evaluation of Caco-2 cells membrane permeability] are shown in Table 1-2.

Comparative Example 8

A mixture of PMF90 (manufactured by Okinawa Research Center Co., Ltd.) as a poorly water-soluble substance and mGHes in a proportion of 25% by mass and 75% by mass, respectively, was evaluated. The results of [Evaluation of solubility over time] and [Evaluation of Caco-2 cells membrane permeability] are shown in Table 1-2.

Comparative Example 9

A mixture of PMF90 (manufactured by Okinawa Research Center Co., Ltd.) as a poorly water-soluble substance and αG hesperidin PA-T in a proportion of 25% by mass and 75% by mass, respectively, was evaluated. The results of [Evaluation of solubility over time] and [Evaluation of Caco-2 cells membrane permeability] are shown in Table 1-2.

[Transferability of Nobiletin into Blood Circulation During Oral Administration to Mice]

Figure 7:
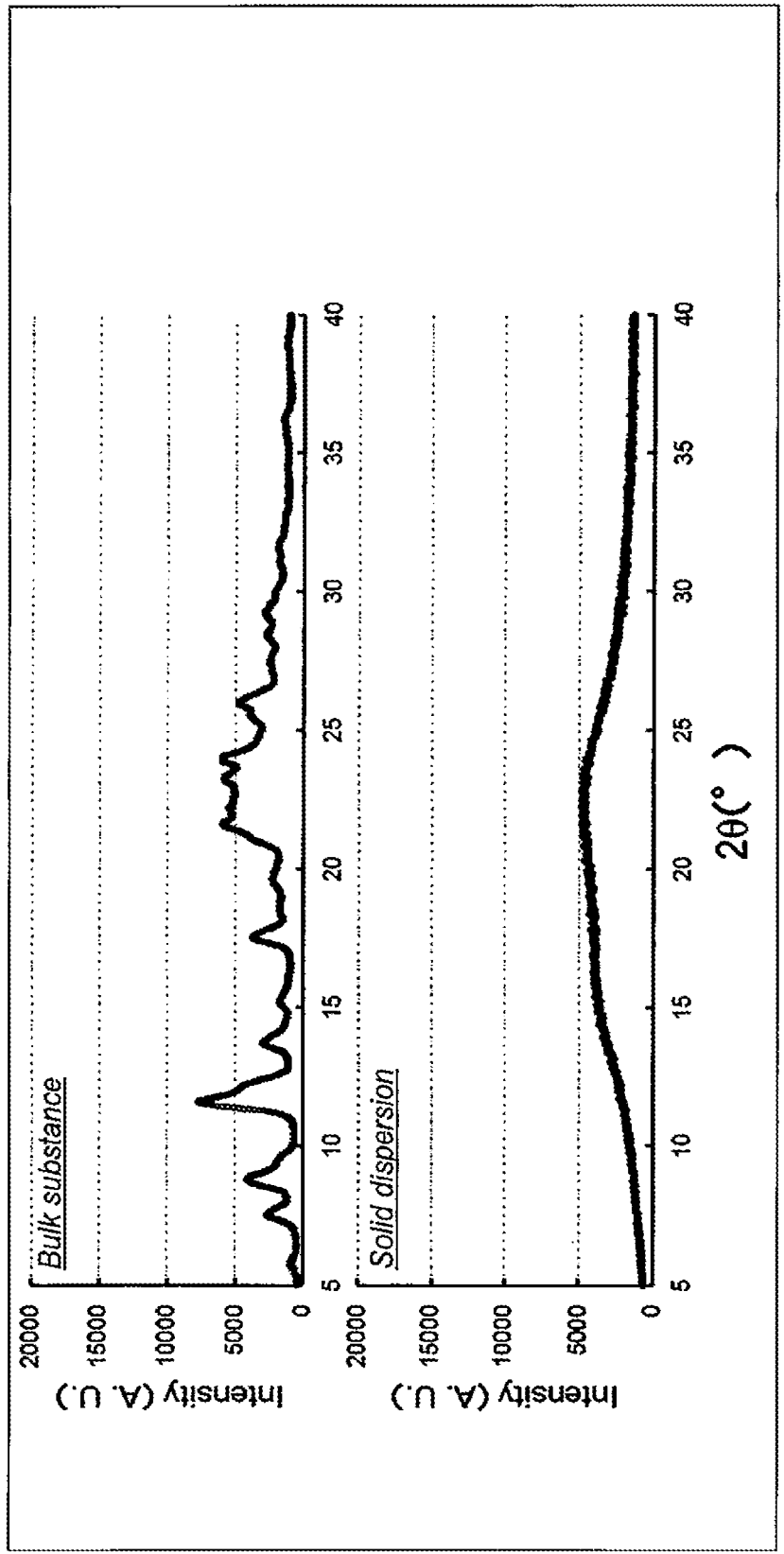
FIG. 7 is a diagram illustrating the results of PMF90 (upper graph) and PMF90-methyl hesperidin solid dispersion (lower graph) according to Example 7 in powder X-ray diffraction.

In the transferability of nobiletin into blood circulation during oral administration of nobiletin, the composition according to Comparative Example 5, and the composition according to Example 1 to mice, nobiletin blood concentration transition to 180 minutes after the administration is shown in FIG. 7, and the maximum blood concentration (Cmax) and the area under the curve (AUC) in the blood concentration transition curve are shown in Table 2. Cmax=3.7 μg/mL (60 minutes after the administration) and AUC=323 μg/(mL·min) in nobiletin bulk substance and Cmax=11.1 μg/mL (30 minutes after the administration), AUC=956 μg/(mL·min) in the composition according to Comparative Example 5. In contrast, Cmax=36.4 μg/mL (30 minutes after the administration) and AUC=3,550 μg/(mL·min) in the composition according to Example 1, that is, the solid dispersion, showing a significant increase in the amount transferred into blood circulation.

[Transferability of Nobiletin into Tissues During Oral Administration to Mice]

In the transferability of nobiletin into tissues during oral administration of nobiletin, the composition according to Comparative Example 5, and the composition according to Example 1 to mice, the amounts of nobiletin transferred in tissues after 30 minutes from the administration are shown in Table 2. Compared to the nobiletin bulk substance and the composition according to Comparative Example 5, the composition according to Example 1, that is, the solid dispersion shows a significant increase in the amount transferred into the tissues examined.

TABLE 1-1

| | | | Example 1 | Example 2 | Example 3 | Example 4 | Example 5 | Example 6 |
|---|---|---|---|---|---|---|---|---|
| Raw materials | Poorly water-soluble substance | | Nobiletin | Nobiletin | Nobiletin | Nobiletin | Nobiletin | Nobiletin |
| | Solubility in water at 25° C. | [ppm] | 1 | 1 | 1 | 1 | 1 | 1 |
| | Aid | | MeHas | MeHas | MeHas | MeHas | MeHas | MeHas |
| | Proportion of poorly water-soluble substance | [% by mass] | 25% | 10% | 15% | 20% | 33% | 40% |
| | Proportion of nobiletin | [% by mass] | 25% | 10% | 15% | 20% | 33% | 40% |
| Treatment conditions | Heating temperature | [° C.] | 130 | 130 | 130 | 130 | 130 | 130 |
| | Heating time | [min] | 10 | 10 | 10 | 10 | 10 | 10 |
| | The number of rotations of extruder screw | [r/min] | 80 | 80 | 80 | 80 | 80 | 80 |
| | Extruder torque | [N·m] | 0.12 | 0.12 | 0.12 | 0.12 | 0.12 | 0.12 |
| | Cooling temperature | [° C.] | 25 | 25 | 25 | 25 | 25 | 25 |
| | Cooling time | [min] | 3 | 3 | 3 | 3 | 3 | 3 |
| | Cooling rate | [° C./sec] | 0.52 | 0.52 | 0.52 | 0.52 | 0.52 | 0.52 |
| Evaluation results | Solubility over time of poorly water-soluble substance (area under curve) | [ppm·min] | 2.20E+05 | 1.19E+05 | 1.78E+05 | 2.07E+05 | 1.14E+05 | 7.15E+04 |
| | Evaluation of cell membrane permeability Concentration of poorly water-soluble substance at start of evaluation of upper portion of insert | [μM] | 132 | 29 | 25 | 25 | 49 | 96 |
| | Evaluation of cell membrane permeability Concentration of poorly | [μM] | 4.33 | 1.25 | 1.04 | 1.16 | 1.35 | 4.27 |

TABLE 1-1-continued

|  |  |  | Example 1 | Example 2 | Example 3 | Example 4 | Example 5 | Example 6 |
|---|---|---|---|---|---|---|---|---|
|  | water-soluble substance at end of evaluation of lower portion of insert Evaluation of cell membrane permeability Standard deviation of concentration of poorly water-soluble substance at end of evaluation of lower portion of insert | [µM] | 0.20 | 0.09 | 0.31 | 0.17 | 0.10 | 0.23 |
|  | Evaluation of cell survival rate in LDH Assay | [%] | 91.0 | 92.6 | 94.3 | 94.3 | 92.1 | 93.1 |
|  | Standard deviation in evaluation of cell survival rate in LDH Assay | [%] | 0.0 | 0.0 | 0.4 | 1.2 | 0.6 | 0.3 |

|  |  |  | Example 7 | Example 8 | Example 9 | Example 10 | Example 11 |
|---|---|---|---|---|---|---|---|
| Raw materials | Poorly water-soluble substance | | PMF90 | PMF90 | PMF90 | PMF90 | PMF90 |
|  | Solubility in water at 25° C. | [ppm] | 1 | 1 | 1 | 1 | 1 |
|  | Aid | | MeHas | MeHas | MeHas | MeHas | MeHas |
|  | Proportion of poorly water-soluble substance | [% by mass] | 25% | 10% | 33% | 40% | 60% |
|  | Proportion of nobiletin | [% by mass] | 15% | 8% | 20% | 24% | 36% |
| Treatment conditions | Heating temperature | [° C.] | 130 | 130 | 130 | 130 | 130 |
|  | Heating time | [min] | 10 | 10 | 10 | 10 | 10 |
|  | The number of rotations of extruder screw | [r/min] | 80 | 80 | 80 | 80 | 80 |
|  | Extruder torque | [N·m] | 0.12 | 0.12 | 0.12 | 0.12 | 0.12 |
|  | Cooling temperature | [° C.] | 25 | 25 | 25 | 25 | 25 |
|  | Cooling time | [min] | 3 | 3 | 3 | 3 | 3 |
|  | Cooling rate | [° C./sec] | 0.52 | 0.52 | 0.52 | 0.52 | 0.52 |
| Evaluation results | Solubility over time of poorly water-soluble substance (area under curve) | [ppm·min] | 1.61E+05 | 7.15E+04 | 1.69E+05 | 1.35E+05 | 7.63E+04 |
|  | Evaluation of cell membrane permeability Concentration of poorly water-soluble substance at start of evaluation of upper portion of insert | [µM] | 66 | 35 | 73 | 66 | 39 |
|  | Evaluation of cell membrane permeability Concentration of poorly water-soluble substance at start of evaluation of upper portion of insert | [µM] | 3.00 | 1.14 | 3.35 | 1.23 | 1.03 |
|  | Evaluation of cell membrane permeability Standard deviation of concentration of poorly water-soluble substance at end of evaluation of lower portion insert | [µM] | 0.14 | 0.06 | 0.26 | 0.26 | 0.06 |
|  | Evaluation of cell survival rate in LDH Assay | [%] | 92.9 | 92.7 | 93.2 | 93.3 | 93.4 |
|  | Standard deviation in evaluation of cell survival rate in LDH Assay | [%] | 2.4 | 0.2 | 0.2 | 0.3 | 0.2 |

|  |  |  | Example 12 | Example 13 | Example 14 | Example 15 | Example 16 |
|---|---|---|---|---|---|---|---|
| Raw materials | Poorly water-soluble substance | | PMF90 | PMF90 | PMF90 | PMF90 | PMF90 |
|  | Solubility in water at 25° C. | [ppm] | 1 | 1 | 1 | 1 | 1 |
|  | Aid | | MeHas | mGHas | mGHas | αGHes PA-T | αGHes PA-T |
|  | Proportion of poorly water-soluble substance | [% by mass] | 87% | 25% | 33% | 25% | 33% |
|  | Proportion of nobiletin | [% by mass] | 40% | 15% | 20% | 15% | 20% |
| Treatment conditions | Heating temperature | [° C.] | 130 | 130 | 130 | 130 | 130 |
|  | Heating time | [min] | 10 | 10 | 10 | 10 | 10 |
|  | The number of rotations of extruder screw | [r/min] | 80 | 80 | 80 | 80 | 80 |
|  | Extruder torque | [N·m] | 0.12 | 0.12 | 0.12 | 0.12 | 0.12 |
|  | Cooling temperature | [° C.] | 25 | 25 | 25 | 25 | 25 |
|  | Cooling time | [min] | 3 | 3 | 3 | 3 | 3 |
|  | Cooling rate | [° C./sec] | 0.52 | 0.52 | 0.52 | 0.52 | 0.52 |
| Evaluation results | Solubility over time of poorly water-soluble substance (area under curve) | [ppm·min] | 6.97E+04 | 1.08E+05 | 7.76E+04 | 9.19E+04 | 6.05E+04 |
|  | Evaluation of cell membrane permeability Concentration of poorly water-soluble substance | [µM] | 43 | 81 | 59 | 134 | 70 |

TABLE 1-1-continued

|  |  | | | | | |
|---|---|---|---|---|---|---|
| at start of evaluation of upper portion of insert | | | | | | |
| Evaluation of cell membrane permeability Concentration of poorly water-soluble substance at end of evaluation of lower portion of insert | [μM] | 1.94 | 3.13 | 1.58 | 3.92 | 1.94 |
| Evaluation of cell membrane permeability Standard deviation of concentration of poorly water-soluble substance at end of evaluation of lower portion insert | [μM] | 0.15 | 0.25 | 0.09 | 0.21 | 0.23 |
| Evaluation of cell survival rate in LDH Assay | [%] | 93.2 | 91.5 | 93.6 | 89.3 | 93.4 |
| Standard deviation in evaluation of cell survival rate inLDH Assay | [%] | 0.2 | 2.2 | 0.2 | 3.4 | 0.2 |

TABLE 1-2

| | | | Comparative Example 1 | Comparative Example 2 | Comparative Example 3 | Comparative Example 4 | Comparative Example 5 |
|---|---|---|---|---|---|---|---|
| Raw materials | Poorly water-soluble substance | | Ellagic acid | Ellagic acid | Sesamin | Hesperidin | Nobiletin |
| | Solubility in water at 25° C. | [ppm] | 4 | 4 | 0.14 | 0.5 | 1 |
| | Aid | | MeHes | MeHes | MeHes | MeHes | MeHes |
| | Proportion of poorly water-soluble substance | [% by mass] | 25% | 25% | 25% | 25% | 25% |
| | Proportion of nobiletin | [% by mass] | — | — | — | — | 25% |
| Treatment conditions | Heating temperature | [° C.] | 160 | 180 | 160 | 160 | No melting treatment by heating |
| | Heating time | [min] | 10 | 10 | 10 | 10 | |
| | The number of rotations of extruder screw | [r/min] | 80 | 80 | 80 | 80 | |
| | Extruder torque | [N · m] | 0.15 | 0.12 | 0.10 | 0.10 | |
| | Cooling temperature | [° C.] | 25 | 25 | 25 | 25 | |
| | Cooling time | [min] | 3 | 3 | 3 | 3 | |
| | Cooling rate | [° C./sec] | 0.52 | 0.52 | 0.52 | 0.52 | |
| Evaluation results | Solubility over time of poorly water-soluble substance (area under curve) | [ppm · min] | 7.27E+04 | 6.78E+04 | 2.67E+03 | 2.22E+04 | 1.76E+04 |
| | Evaluation of cell membrane peermeability Concentration of poorly water-soluble substance at start of evaluation of upper portion of insert | [μM] | 6.90 | 0.06 | 8.60 | 4.00 | 17.53 |
| | Evaluation of cell membrane permeability Concentration of poorly water-soluble substance at end of evaluation of lower portion of insert | [μM] | 0.03 | 0.00 | 0.37 | 0.02 | 0.24 |
| | Evaluation of cell membrane permeability Standard deviation of concentration of poorly water-soluble substance at end of evaluation of lower portion of insert | [μM] | 0.01 | 0.04 | 0.01 | 0.04 | 0.03 |
| | Evaluation of cell survival rate in LDH Assay | [%] | 90.6 | 89.5 | 92.7 | 86.6 | 94.4 |
| | Standard deviation in evaluation of cell survival rate in LDH Assay | [%] | 0.0 | 0.0 | 0.0 | 0.0 | 0.0 |

| | | | Comparative Example 6 | Comparative Example 7 | Comparative Example 8 | Comparative Example 9 |
|---|---|---|---|---|---|---|
| Raw materials | Poorly water-soluble substance | | PMF90 | PMF90 | PMF90 | PMF90 |
| | Solubility in water at 25° C. | [ppm] | 1 | 1 | 1 | 1 |
| | Aid | | MeHes | MeHes | mGHes | aGHes PA-T |
| | Proportion of poorly water-soluble substance | [% by mass] | 25% | 40% | 25% | 25% |
| | Proportion of nobiletin | [% by mass] | 15% | 24% | 15% | 15% |
| Treatment conditions | Heating temperature | [° C.] | No melting treatment by heating | No melting treatment by heating | No melting treatment by heating | No melting treatment by heating |
| | Heating time | [min] | | | | |
| | The number of rotations of extruder screw | [r/min] | | | | |
| | Extruder torque | [N · m] | | | | |
| | Cooling temperature | [° C.] | | | | |
| | Cooling time | [min] | | | | |
| | Cooling rate | [° C./sec] | | | | |
| Evaluation results | Solubility over time of poorly water-soluble substance (area under curve) | [ppm · min] | 1.44E+04 | 3.10E+04 | 4.56E+04 | 3.76E+04 |
| | Evaluation of cell membrane peermeability Conccentration of poorly water-soluble substance at start of evaluation of upper portion of insert | [μM] | 51 | 36.9 | 24.5 | 29.5 |

TABLE 1-2-continued

| | | | | | |
|---|---|---|---|---|---|
| Evaluation of cell membrane permeability Concentration of poorly water-soluble substance at end of evaluation of lower portion of insert | [µM] | 1.91 | 1.30 | 0.66 | 0.76 |
| Evaluation of cell membrane permeability Standard deviation of concentration of poorly water-soluble substance at end of evaluation of lower portion of insert | [µM] | 0.05 | 0.08 | 0.04 | 0.09 |
| Evaluation of cell survival rate in LDH Assay | [%] | 94.5 | 42.1 | 93.1 | 95.2 |
| Standard deviation in evaluation of cell survival rate in LDH Assay | [%] | 1.5 | 15.0 | 4.7 | 1.3 |

TABLE 1

| Sample name | Cmax (µg/mL) | AUC (µg/(mL · min)) |
|---|---|---|
| Nobiletin | 3.7 (60 minutes after administration) | 323 |
| Composition according to Comparative Example 5 | 11.1 (30 minutes after administration) | 956 |
| Composition according to Example 1 | 36.4 (10 minutes after administration) | 3550 |

TABLE 2

| Sample name | Liver (µg/mg of tissue) | White adipose tissue (µg/mg of tissue) | Brown adipose tissue (µg/mg of tissue) | Gastrocnemius (µg/mg of tissue) | Soleus muscle (µg/mg of tissue) |
|---|---|---|---|---|---|
| Nobiletin | 238 | 149 | 199 | 16.6 | 14.7 |
| Composition according to Comparative Example 5 | 818 | 713 | 674 | 61.6 | 81.0 |
| Composition according to Example 1 | 1910 | 1800 | 1230 | 284 | 429 |

| Sample name | Shin bone (µg/mg of tissue) | Thighbone (µg/mg of tissue) | Left brain (µg/mg of tissue) | Brain cortex (µg/mg of tissue) | Hippocampus (µg/mg of tissue) |
|---|---|---|---|---|---|
| Nobiletin | 1.75 | 7.89 | 17.4 | 11.6 | 35.3 |
| Composition according to Comparative Example 5 | 7.56 | 10.6 | 59.2 | 45.7 | 67.2 |
| Composition according to Example 1 | 37.1 | 50.4 | 314 | 269 | 376 |

Figure 23:
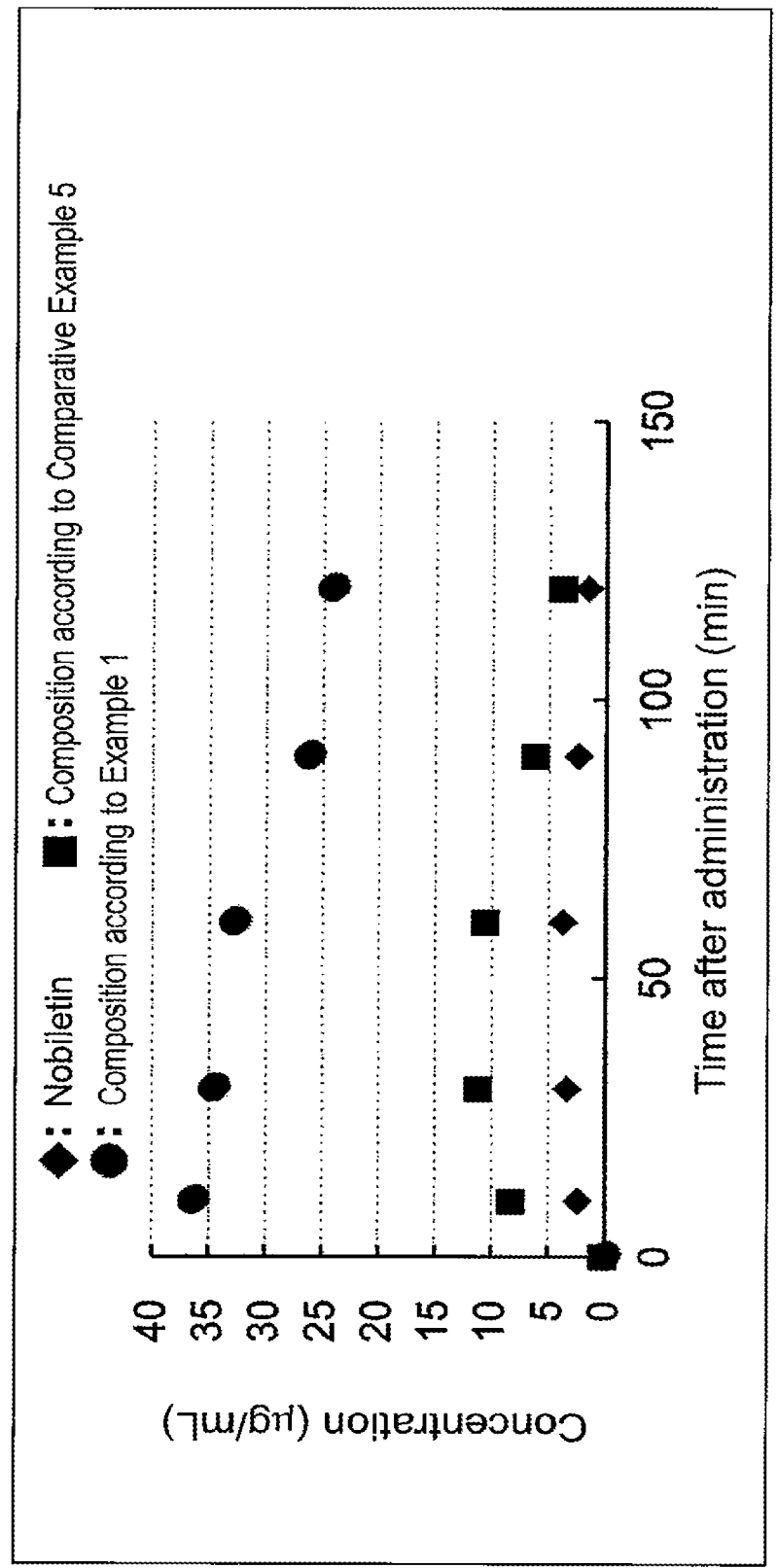
FIG. 23 is a diagram illustrating the transition of the nobiletin blood concentration from the administration up to 180 minutes when nobiletin is orally administered to mice in evaluation of the transferability of nobiletin into blood circulation.

From the results shown above, the nobiletin-containing solid dispersion had significantly high solubility over time of nobiletin, for example, 2.20×10⁵ ppm·min in Example 1, and a high concentration of nobiletin dissolved was maintained for a long time (Table 1-1 and FIG. 23).

It is inferred that the presence of specific intermolecular interaction of nobiletin-methyl hesperidin in the solid dispersion and aqueous solution results in such high solubility, compared to the solid dispersions prepared by mixing hesperidin, sesamin, or ellagic acid, which is known as a polyphenol having poor solubility similar to that of nobiletin, with methyl hesperidin.

The nobiletin-containing solid dispersion also has significantly high permeability to the cell membrane derived from human small intestine epithelial cells. It is inferred that the significantly high ability of the water-soluble hesperidin derivative to solve nobiletin and further the supersaturation phenomenon of nobiletin expressed in a high concentration for a long time result in such high permeability, compared to the solid dispersions of other poorly soluble polyphenols described above. A variety of compounds classified into Class 4 in Biopharmaceutical Classification System (BCS), even if having high solubility, do not demonstrate such improved cell membrane permeability and oral absorption. The same solution prepared by the same method was added to the upper portion of the insert in the evaluation of cell membrane permeability in all of Examples and Comparative Examples. Accordingly, it is believed that this high solubility of nobiletin attains the significantly high cell membrane permeability of nobiletin in the solid dispersion, and further attains high transferability into blood circulation and transferability into tissues in the experiment of oral administration in an animal.

Accordingly, it is expected that the oral absorption of nobiletin is enhanced by use of the nobiletin-containing solid dispersion according to the present invention.

The invention claimed is:

1. A method for producing a solid dispersion comprising nobiletin, comprising:
   mixing nobiletin or a nobiletin-containing product with a water-soluble hesperidin derivative, and then melting the mixture by heating; and
   solidifying the melted product by cooling, wherein the water-soluble hesperidin derivative is methyl hesperidin.

2. The method for producing a solid dispersion according to claim 1, wherein a heating temperature is from 95 to 200° C.

3. The method for producing a solid dispersion according to claim 1, wherein a heating temperature is from 95 to 180° C.

4. The method for producing a solid dispersion according to claim 1, wherein a mass ratio of nobiletin to the water-soluble hesperidin derivative [nobiletin/water-soluble hesperidin derivative] is in a range from 0.01 to 0.67 during mixing of nobiletin or a nobiletin-containing product with the water-soluble hesperidin derivative.

5. The method for producing a solid dispersion according to claim 1, wherein the mixing of nobiletin or a nobiletin-containing product with the water-soluble hesperidin derivative, and then melting the mixture by heating, is performed using an extruder including a screw.

6. The method for producing a solid dispersion according to claim 1, wherein a content of nobiletin in the mixture is 5 to 50% by mass.

7. The method for producing a solid dispersion according to claim 1, wherein a content of nobiletin in the mixture is 7.5 to 45% by mass.

8. The method for producing a solid dispersion according to claim 1, wherein a content of nobiletin in the mixture is 10 to 40% by mass.

9. The method for producing a solid dispersion according to claim 1, wherein a content of nobiletin in the mixture is 15 to 35% by mass.

10. The method for producing a solid dispersion according to claim 1, wherein a content of methyl hesperidin in the mixture is 10 to 99% by mass.

11. The method for producing a solid dispersion according to claim 1, wherein a content of methyl hesperidin in the mixture is 30 to 92.5% by mass.

12. The method for producing a solid dispersion according to claim 1, wherein a content of methyl hesperidin in the mixture is 45 to 90% by mass.

13. The method for producing a solid dispersion according to claim 1, wherein a content of methyl hesperidin in the mixture is 60 to 85% by mass.

14. The method for producing a solid dispersion according to claim 1, wherein a content of methyl hesperidin in the mixture is 65 to 85% by mass.

15. The method for producing a solid dispersion according to claim 1, wherein the mixture further comprises at least one sugar or sugar alcohol selected from the group consisting of glucose, fructose, maltose, mannose, rhamnose, ribose, xylose, trehalose, xylitol, mannitol, erythritol, arabinose, inositol, glucosamine, sucralose, and sorbitol.

16. The method for producing a solid dispersion according to claim 1, wherein the mixture further comprises at least one polymer selected from the group consisting of linseed gum, arabic gum, arabinogalactan, welan gum, *cassia* gum, ghatti gum, curdlan, carrageenan, xanthan gum, chitin, chitosan, guar gum, gellan gum, cyclodextrin, tamarind seed gum, tara gum, tragacanth gum, microcrystal cellulose, microfibrous cellulose, nisin, pullulan, pectin, macrophomopsis gum, rhamsan gum, acetylated adipic acid-crosslinked starch, acetylated oxidized starch, acetylated phosphoric acid-crosslinked starch, alginic acid and a salt thereof, starch sodium octenylsuccinate, casein and a salt thereof, carboxymethyl cellulose and a salt thereof, chondroitin sodium sulfate, hydroxypropylated phosphoric acid-crosslinked starch, hydroxypropyl cellulose, hydroxypropyl starch, hydroxypropyl methyl cellulose, methyl cellulose, phosphoric acid-crosslinked starch, phosphorylated starch; sodium polyacrylate, polyvinylpyrrolidone, and polyvinylpolypyrrolidone.

17. A nobiletin-containing solid dispersion obtained by the method according to claim 1, wherein nobiletin has a degree of crystallization of 10% or less as calculated from an X-ray diffraction spectrum.

* * * * *